United States Patent
Hirayama

(10) Patent No.: US 11,559,187 B2
(45) Date of Patent: Jan. 24, 2023

(54) MULTISTAGE PUSHBUTTON SWITCH DEVICE AND MULTISTAGE PUSHBUTTON SWITCH DEVICE FOR ENDOSCOPE

(71) Applicant: HOYA CORPORATION, Tokyo (JP)

(72) Inventor: Tetsu Hirayama, Tokyo (JP)

(73) Assignee: HOYA CORPORATION, Tokyo (JP)

(*) Notice: Subject to any disclaimer, the term of this patent is extended or adjusted under 35 U.S.C. 154(b) by 990 days.

(21) Appl. No.: 15/775,227

(22) PCT Filed: Nov. 7, 2016

(86) PCT No.: PCT/JP2016/082968
§ 371 (c)(1),
(2) Date: May 10, 2018

(87) PCT Pub. No.: WO2017/082204
PCT Pub. Date: May 18, 2017

(65) Prior Publication Data
US 2018/0325358 A1    Nov. 15, 2018

(30) Foreign Application Priority Data
Nov. 13, 2015   (JP) .............................. JP2015-223422

(51) Int. Cl.
*A61B 1/00*        (2006.01)
*H01H 13/50*    (2006.01)
(Continued)

(52) U.S. Cl.
CPC ............ *A61B 1/00066* (2013.01); *A61B 1/00* (2013.01); *A61B 1/015* (2013.01); *G02B 23/24* (2013.01);
(Continued)

(58) Field of Classification Search
CPC .................. H01H 13/503; A61B 1/015; A61B 2017/00393
See application file for complete search history.

(56) References Cited

U.S. PATENT DOCUMENTS 4,029,924 A  *  6/1977  Frank .................. H01H 13/503
                                                                    200/290
2006/0041190 A1    2/2006  Sato
2008/0262307 A1   10/2008  Kakuto et al.

FOREIGN PATENT DOCUMENTS

JP    S59-99621 A    6/1984
JP    H07-220555 A   8/1995
(Continued)

OTHER PUBLICATIONS

International Search Report issued in PCT Patent Application No. PCT/JP2016/082968, dated Jan. 10, 2017.
(Continued)

*Primary Examiner* — Alexandra L Newton
*Assistant Examiner* — Rynae E Boler
(74) *Attorney, Agent, or Firm* — Greenblum & Bernstein, P.L.C.

(57) ABSTRACT

In a multistage pushbutton switch device, n pushbutton switches and at least one load absorption spring are movably arranged in between a pushbutton member and a reaction force wall in the same axial line, each of the n pushbutton switches is composed of an electrical switch member and a pressing member that operates the electrical switch member, and (n−1) that is one less than n, or more pushbutton switches is arranged with an intermediate spring member, when the pushbutton member is pressed and displaced, the n electrical switch members are sequentially turned on, the load absorption spring is arranged in at least one of between the pushbutton member and the pushbutton switch that is the nearest to the pushbutton member, between pushbutton
(Continued)

switches that are adjacent, and between the reaction force wall and the pushbutton switch that is the nearest to the reaction force wall.

20 Claims, 15 Drawing Sheets

(51) Int. Cl.
 *G02B 23/24* (2006.01)
 *A61B 1/015* (2006.01)
 *A61B 17/00* (2006.01)
(52) U.S. Cl.
 CPC ....... *H01H 13/503* (2013.01); *A61B 1/00091* (2013.01); *A61B 2017/00393* (2013.01); *A61B 2017/00415* (2013.01); *H01H 2300/014* (2013.01)

(56) References Cited

FOREIGN PATENT DOCUMENTS

| JP | H10-225434 A | 8/1998 | |
|----|----|----|----|
| JP | H11-032979 A | 2/1999 | |
| JP | 2007-188797 A | 7/2007 | |
| JP | 2007188797 A * | 7/2007 | ......... A61B 1/00039 |
| WO | 2007/080723 A1 | 7/2007 | |

OTHER PUBLICATIONS

International Preliminary Report on Patentability issued in PCT Patent Application No. PCT/JP2016/082968, dated May 15, 2018.
Office Action issued in European Patent Office (EPO) Counterpart Patent Appl. No. 16864165.2, dated Mar. 23, 2022.

* cited by examiner

FIG. 4A

| PRESSING | FUNCTION | SW1 | SW2 | V1 | V2 | V3 |
|---|---|---|---|---|---|---|
| WAIT | NONE | OFF | OFF | CLOSE | CLOSE | OPEN |
| ONE-STAGE PRESSING | AIR SUPPLY | ON | OFF | OPEN | CLOSE | OPEN |
| TWO-STAGE PRESSING | WATER SUPPLY | ON | ON | CLOSE | OPEN | CLOSE |

FIG. 4B

| PRESSING | FUNCTION | SW1 | SW2 | V1 | V2 | V3 |
|---|---|---|---|---|---|---|
| WAIT | NONE | OFF | OFF | CLOSE | CLOSE | OPEN |
| ONE-STAGE PRESSING | AIR SUPPLY | ON | OFF | OPEN | CLOSE | OPEN |
| TWO-STAGE PRESSING | SPRAYING | ON | ON | OPEN | OPEN | CLOSE | ial
MULTISTAGE PUSHBUTTON SWITCH DEVICE AND MULTISTAGE PUSHBUTTON SWITCH DEVICE FOR ENDOSCOPE

CROSS-REFERENCE TO RELATED APPLICATIONS

This application is the national phase under 35 U.S.C. § 371 of PCT International Application No. PCT/JP2016/082968 which has an International filing date of Nov. 7, 2016 and designated the United States of America.

FIELD

The present invention relates to a multistage pushbutton switch device that sequentially operates a plurality of electrical switches, by pressing operation of a single pushbutton member. The present invention particularly relates to a multistage pushbutton switch device for an endoscope, that is suitable for being used in an endoscope that sequentially performs any two or more operations of air supply, water supply, and spraying, from a discharge nozzle opened in a tip end of an intracorporeal insertion portion.

BACKGROUND

In a general endoscope, at least one discharge nozzle is opened in a tip end of an insertion portion extending from a control body. From this discharge nozzle, any of air, water, and mist (a mixture of air and water) is sprayed, and operations such as washing of a surface of an objective lens, and air supply to a body cavity is performed. Conventionally, an air supply and water supply switching device is arranged in the control body, for causing the discharge nozzle to perform any two or more operations of air supply, water supply, and spraying (for example, refer to Japanese Patent Application Laid-Open No. H10-225434, hereinafter, referred to as Patent Document 1). This air supply and water supply switching device has a basic structure of changing a press displacement position of a piston body slidably fit into a cylinder, to switch a flow path of air supply and water supply opened in the cylinder.

On the other hand, a multistage pushbutton switch device that operates a switch that controls a solenoid valve to open and close, by pressing operation of a pushbutton, to perform the plurality of operations, is proposed (refer to Japanese Patent Application Laid-Open No. H11-032979 and 2007-188797, hereinafter, referred to as Patent Document 2 and 3).

SUMMARY

When an air supply and water supply switching device as Patent Document 1 is provided in a control body, a structure of the control body becomes complex, and assembly cost and weight are increased. Conventional air supply and water supply switching devices are assumed to be provided in a control body, and practically cannot be operated other person than an operator who operates an endoscope. In the pushbutton switch device of Patent Document 2, a plurality of switches are arrayed in parallel to be sequentially operated by pistons having different lengths that are displaced by a single pushbutton. Thus, a large space is required in below the pushbutton, and downsizing is difficult. An object of the pushbutton switch device of Patent Document 3 is to prevent deformation movement of a lead wire and operation failure due to the deformation movement, by fixing mechanical positions of first and second switches that are pressing operated by a pushbutton member. Thus, fixation structures of the first and second switches must be complex, and since a pressing force acting on a pushbutton is directly applied to the switches, loads to the switches vary significantly, and operation failure may occur.

An object of the present disclosure is to acquire a multistage pushbutton switch device that can prevent an excessive load to an electrical switch, the multistage pushbutton switch device being a type of performing any two or more operations of air supply, water supply, and spraying, by operating an electrical switch that controls a solenoid valve to open and close, by pressing operation of a pushbutton.

In addition, an object of the present disclosure is to acquire a multistage pushbutton switch device that can prevent an excessive load to an electrical switch, the multistage pushbutton switch device capable of sequentially operating a plurality of electrical switches by pressing operation of a single pushbutton member, not only for an endoscope.

The present inventor has recognized that Patent Document 3 has a premise that a plurality of electrical switches are fixed and provided, and this ends up in causing a support structure around the electrical switches to be complex. Thus, the present inventor has made the present disclosure on the basis of a viewpoint that a multistage pushbutton switch device having a simple configuration can be acquired by a configuration in which at least one electrical switch is supported so as to move in conjunction with pressing operation of a pushbutton.

A multistage pushbutton switch device according to the present disclosure has: a pushbutton member that is energized in a projection direction, and is pressed and displaced against an energizing direction; and a plurality of electrical switch members that are operated by pressing operation of the pushbutton member, wherein n (n is an integer of two or more) pushbutton switches and at least one load absorption spring are arranged in between the pushbutton member and a reaction force wall receiving a reaction force of an energizing means that energizes the pushbutton member, in the same axial line, so that other elements than elements that contact with the reaction force wall are movable, each of the n pushbutton switches is composed of an electrical switch member and a pressing member that operates the electrical switch member, and (n−1) that is one less than n, or more pushbutton switches is arranged with an intermediate spring member that separates the electrical switch member and the pressing member, when the pushbutton member is pressed and displaced, the n electrical switch members are sequentially turned on, by the pressing member that moves to approach the electrical switch member, a stopper that mechanically regulates the maximum press displacement position of the pushbutton member is provided, the load absorption spring is arranged in at least one of between the pushbutton member and the pushbutton switch that is the nearest to the pushbutton member, between pushbutton switches that are adjacent, and between the reaction force wall and the pushbutton switch that is the nearest to the action force wall, and strengths of the (n−1) or more intermediate spring members and the load absorption spring are set so that an electrical switch member that is turned on lastly is turned on before the pushbutton member abuts to the stopper.

It is preferable that the multistage pushbutton switch device of the present disclosure further includes a means that determines an initial elastic force of the intermediate spring member in at least one of the pushbutton switches described above.

The n pushbutton switches can include one pushbutton switch that does not have the intermediate spring member, and (n−1) pushbutton switches that have the intermediate spring member.

All the n pushbutton switches can be pushbutton switches having the intermediate spring member.

In the multistage pushbutton switch device of the present disclosure, n can be n=2 in the simplest.

The present disclosure can be applied to a multistage pushbutton switch device for an endoscope, that includes a solenoid valve that performs any two or more operations of air supply, water supply, and spraying, from a discharge nozzle opened in a tip end of an intracorporeal insertion portion, by on and off of the plurality of electrical switches.

By the multistage pushbutton switch device of the present disclosure, a load applied to an electrical switch can be stable, and even when a pushbutton member is strongly pushed, the load is not increased. Accordingly, a damage due to an excessive pressing force can be prevented. When being applied to a multistage pushbutton switch device of an endoscope, the present disclosure can be installed in another place than an operation unit of the endoscope, and operated by another person than an operator.

The above and further objects and features will more fully be apparent from the following detailed description with accompanying drawings.

BRIEF DESCRIPTION OF THE DRAWINGS

FIG. 4A and FIG. 4B are diagrams illustrating a switching state of air supply, water supply, and spraying by a two-stage pushbutton switch device according to the present disclosure.

FIG. 6A is a vertical cross sectional view and FIG. 6B is a cross sectional view along 6B-6B line of FIG. 6A.

FIG. 9A is a vertical cross sectional view and FIG. 9B is a cross sectional view along 9B-9B line of FIG. 9A.

DETAILED DESCRIPTION

Figure 1:
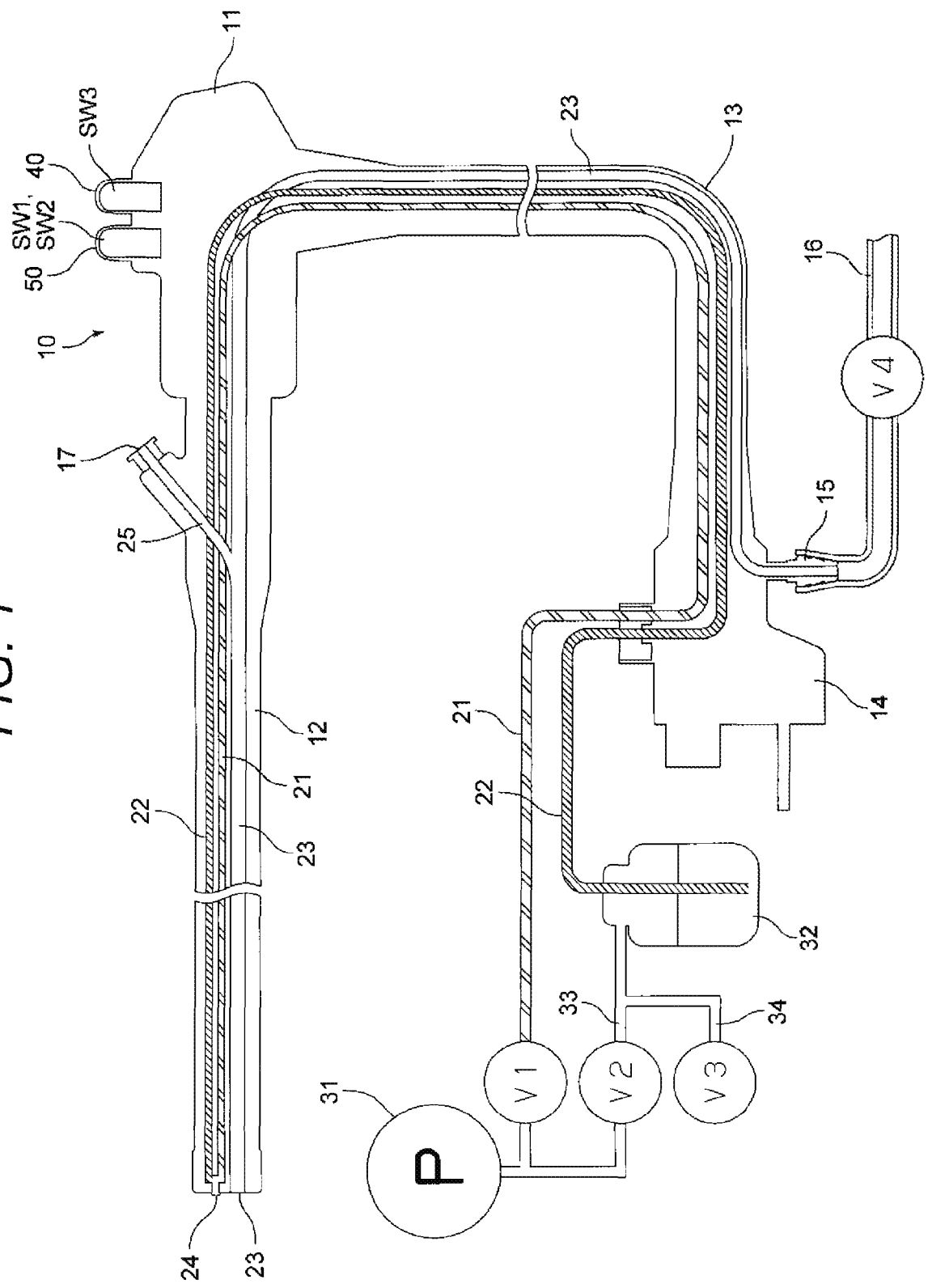
FIG. 1 is a conceptual diagram of an endoscope having a multistage pushbutton switch device to which the present disclosure is applied.

FIG. 1 is a conceptual diagram of an endoscope 10 for medical use to which a multistage pushbutton switch device according to the present disclosure is applied. The endoscope 10 includes: a control body 11; an intracorporeal insertion portion 12 that extends forward from the control body 11; a universal tube 13 that extends rearward from the control body 11; and a connector portion 14 fixed to a rear end of the universal tube 13. The intracorporeal insertion portion 12 has a flexible tube having flexibility, a bending tube, and a tip end rigid portion, in order from the control body 11 side. The bending tube is operated to be bent by operation of a bending control body (not illustrated) provided in the control body 11.

A series of air supply tubes 21, a series of water supply tubes 22, and a series of suction channels 23 are inserted into the intracorporeal insertion portion 12, the control body 11, and the universal tube 13. Tip end portions of the air supply tube 21 and the water supply tube 22 are joined to a single discharge nozzle 24 (see FIG. 2), and opened in a tip end surface (the tip end rigid portion) of the intracorporeal insertion portion 12. In a rear end portion of the air supply tube 21, a projection portion from the universal tube 13 is connected to an air pump 31 via an air supply opening and closing valve (a solenoid valve) V1. In a rear end portion of the water supply tube 22, similarly, a projection portion from the universal tube 13 is introduced into water in a water supply bottle 32. In the water supply bottle 32, compressed air from the air pump 31 is introduced to space above the water surface in the water supply bottle 32, via an air supply passage 33. A water supply opening and closing valve (a solenoid valve) V2 is provided in the air supply passage 33. A pressure release valve (solenoid valve) V3 is provided in a branched passage 34 branched from the air supply passage 33 in the water supply bottle 32 side from the water supply opening and closing valve V2. In FIG. 1, hatching of wide pitches is applied to the air supply tube 21, hatching of narrow pitches is applied to the water supply tube 22, and hatching is not applied to the suction channel 23, so that recognizing (viewing) is facilitated.

A rear end portion of the suction channel 23 is connected to a suction port 15 opened near the connector portion 14. A suction channel 16 having a suction opening and closing valve (a solenoid valve) V4 is connected to the suction port 15. The suction channel 16 is connected to a suction pump (not illustrated). The suction channel 23 is branched as a forceps channel 25 in the intracorporeal insertion portion 12. The forceps channel 25 continues to a forceps inlet 17 of the control body 11.

Figure 2:
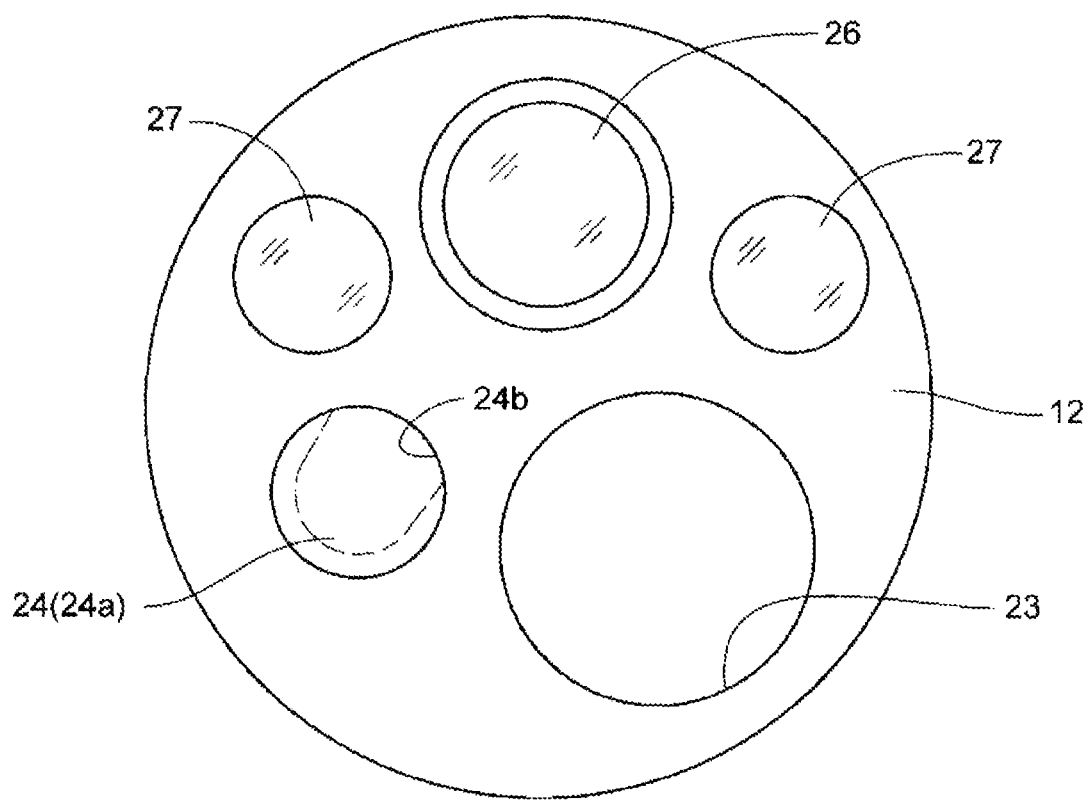
FIG. 2 is a conceptual diagram of a tip end of an insertion portion of the endoscope.

As illustrated in FIG. 2, the discharge nozzle 24 and the suction channel 23 described above are opened in a tip end portion of the intracorporeal insertion portion 12. The discharge nozzle 24 has an end portion closing wall 24a, and an opening portion 24b obtained by opening (removing) part of an objective lens 26 side of the end portion closing wall 24a. Air, water, or mist (mixture of air and water) supplied to the discharge nozzle 24 are supplied to the objective lens 26. In an endoscope not requiring spraying, independent discharge nozzles for the air supply tube 21 and the water supply tube 22 may be provided.

The objective lens 26, and a pair of light distribution lenses 27 sandwiching the objective lens 26 are located in the tip end portion of the intracorporeal insertion portion 12. An image of an inside of a body cavity, formed by the objective lens 26 is formed on an imaging element (not illustrated) in the intracorporeal insertion portion 12, and a video signal of the image is transmitted to a processor (not illustrated) via a movie cable passing the intracorporeal insertion portion 12, the control body 11, the universal tube 13, and the connector portion 14. A light emitting element (not illustrated) is located in a rear surface of the light distribution lens 27. When current is applied from the processor to this light emitting element via a cable passing the connector portion 14, the universal tube 13, the control body 11, and the intracorporeal insertion portion 12, the light emitting element emits light, and illumination light is emitted from the light distribution lens 27.

A suction button device 40 that controls the suction opening and closing valve V4, and a two-stage pushbutton switch device 50 that controls the air supply opening and closing valve V1, the water supply opening and closing valve V2, and the pressure release valve V3, are provided in the control body 11. The suction button device 40 has one electrical switch SW3, and the two-stage pushbutton switch device 50 has two electrical switches SW1 and SW2.

Figure 3:
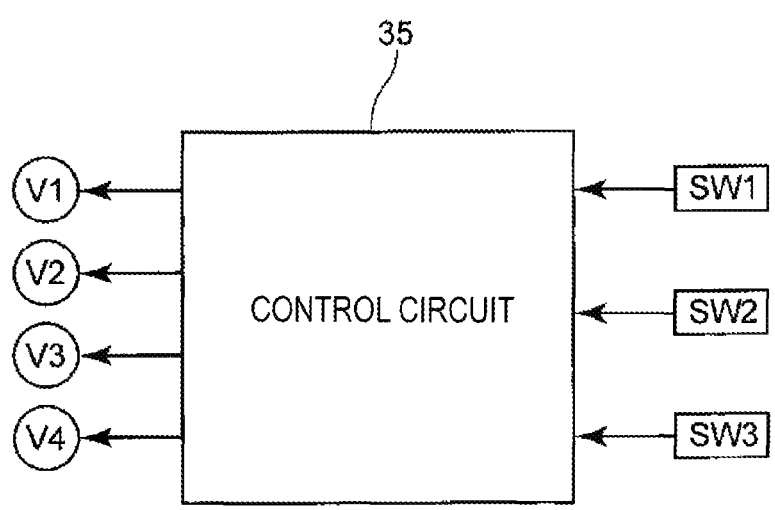
FIG. 3 is a block diagram illustrating a control system of the endoscope of FIG. 1.

FIG. 3 illustrates a configuration of a control system that controls the air supply opening and closing valve V1, the water supply opening and closing valve V2, the pressure release valve V3, and the suction opening and closing valve V4. A control circuit 35 controls the air supply opening and closing valve V1, the water supply opening and closing valve V2, the pressure release valve V3, and the suction opening and closing valve V4 to open and close, in response to on and off of the electrical switches SW1, SW2, SW3.

FIG. 4A and FIG. 4B illustrates an operation (on-off) state of the two electrical switches SW1 and SW2, and an example of opening and closing control of the air supply opening and closing valve V1, the water supply opening and closing valve V2, and the pressure release valve V3. The air supply opening and closing valve V1 and the water supply opening and closing valve V2 are normally closed valves, and the pressure release valve V3 is normally opened valve. In FIG. 4A, the electrical switch SW1 is turned on by one-stage pressing operation of the pushbutton of the two-stage pushbutton switch device 50, and thereby, the air supply opening and closing valve V1 is opened, and the electrical switch SW2 is turned on while the electrical switch SW1 is remained to be on by two-stage pressing operation, and thereby, the air supply opening and closing valve V1 is closed and the water supply opening and closing valve V2 is opened. The pressure release valve V3 is maintained to an opened state by the one-stage pressing operation of the two-stage pushbutton switch device 50, and is closed by the two-stage pressing operation (when the electrical switch SW2 is turned on). Accordingly, as illustrated in FIG. 4A, air is jetted (air is supplied) from the discharge nozzle 24 (the opening portion 24b) by the one-stage pressing operation of the two-stage pushbutton switch device 50, and water is jetted (water is supplied) by the two-stage pressing operation.

A difference of FIG. 4B from FIG. 4A is that the air supply opening and closing valve V1 maintains the opened state when both the electrical switches SW1 and SW2 are turned on by the two-stage pressing operation of the two-stage pushbutton switch device 50. Thus, air is jetted (air is supplied) from the discharge nozzle 24 (the opening portion 24b) by the one-stage pressing operation of the two-stage pushbutton switch device 50, and mist (mixture of air and water) is jetted (sprayed) by the two-stage pressing operation.

Figure 5A:
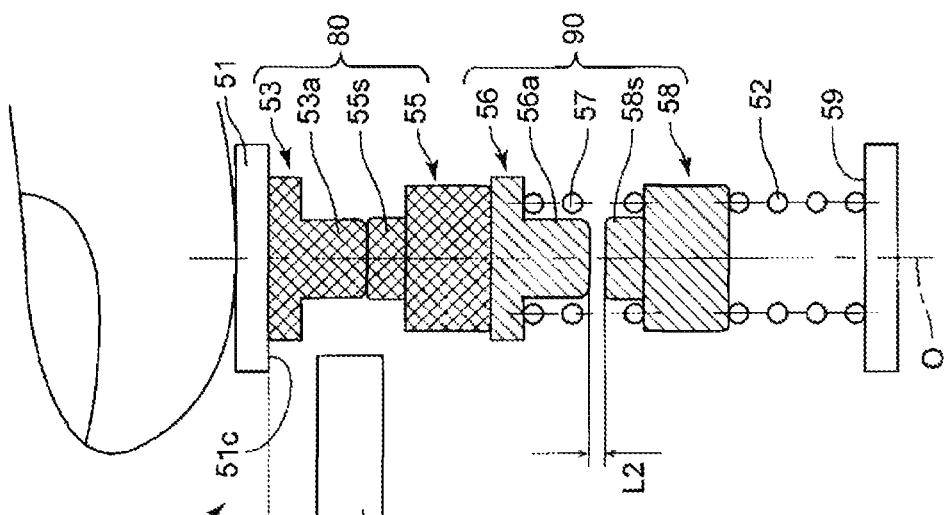
FIG. 5A, FIG. 5B, and FIG. 5C are conceptual diagrams illustrating a first embodiment group in which the present disclosure is applied to the two-stage pushbutton switch device.
Figure 5B:
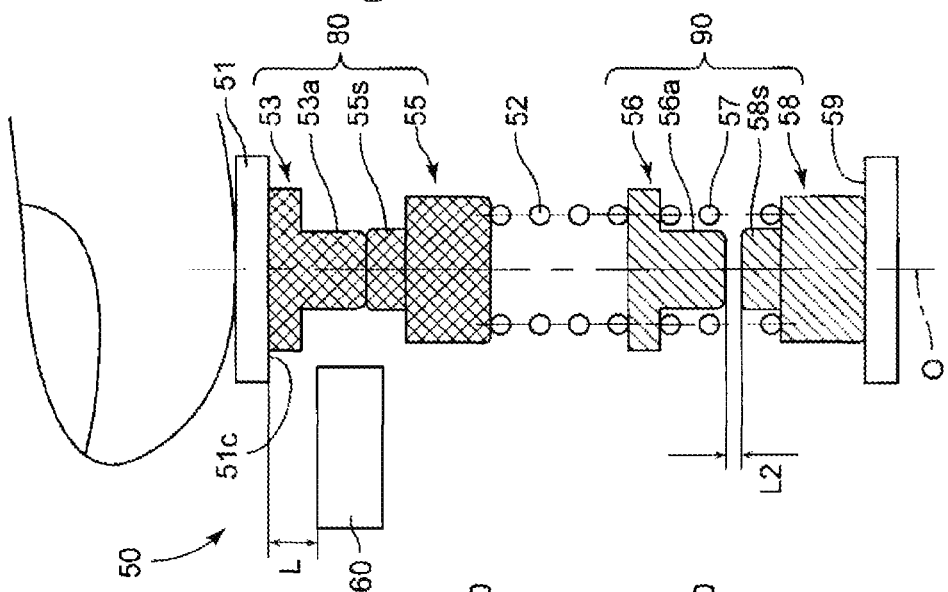
Figure 5C:
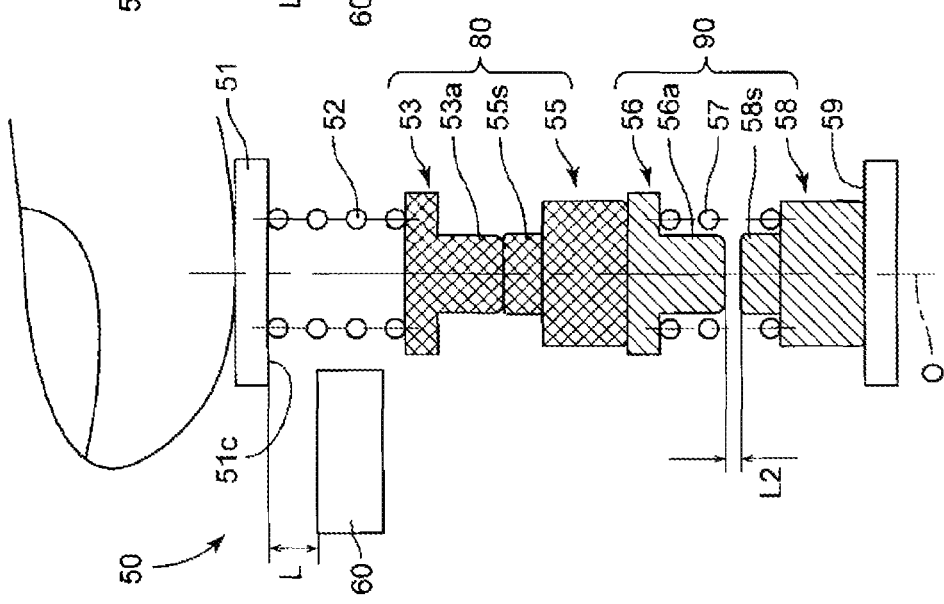

FIG. 5A, FIG. 5B, and FIG. 5C illustrate a first embodiment (group) in which the present disclosure is applied to the two-stage pushbutton switch device 50 that performs on-off operation of the electrical switches SW1 and SW2 described above. First, FIG. 5A will be described. This two-stage pushbutton switch device 50 includes a pushbutton (a pushbutton member) 51, a load absorption spring 52, a first pushbutton switch (an electrical switch unit) 80, a second pushbutton switch (an electrical switch unit) 90, and a reaction force wall (a fixed wall) 59, in order from an upper portion of the drawing, in the same axial line O. Hatching of the same manner is applied to main elements composing the first pushbutton switch 80, and hatching of the same manner that is different from the first pushbutton switch 80 is applied to main elements composing the second pushbutton switch 90, so that discrimination of units is facilitated.

The first pushbutton switch 80 has a first pressing member 53, and a first switch (an electrical switch, an electrical switch member) 55, and the second pushbutton switch 90 has a second pressing member 56, an intermediate spring (an intermediate spring member) 57, and a second switch (an electrical switch, an electrical switch member) 58.

All elements excluding the second switch 58 of the second pushbutton switch 90 located above the reaction force wall 59 are movable in the axial line O direction, and are energized to move upward. A projection position of the pushbutton 51 is regulated by a mechanical stopper (not illustrated), and a pressing position is regulated by a position in which a stopper flange 51c abuts to a pressing position stopper 60. The stopper flange 51c and the pressing position stopper 60 compose a stopper that mechanically regulates the maximum press displacement position of the pushbutton (pushbutton member) 51. Any one of the first switch 55 and the second switch 58 composes the electrical switch SW1 of FIG. 4A, FIG. 4B, and the other composes the electrical switch SW2.

Both the first switch 55 and the second switch 58 are composed of a commercially available tactile switch, are remained to be an off state normally, and are turned on when operation portions 55s, 58s are pushed. A pressing portion 53a in a lower end portion of the first pressing member 53 contacts (faces) with the operation portion 55s of the first switch 55. A pressing portion 56a that contacts (faces) with the operation portion 58s of the second switch 58 is included in the second pressing member 56.

In FIG. 5A, a stroke until the pushbutton 51 in an initial position (projection) state abuts to the pressing position stopper 60 is set as L, a stroke until the second pressing member 56 of the second pushbutton switch 90 turns on the second switch 58 as L2, and L and L2 are set to be L>L2. Strictly, the strokes L, L2 include a stroke (not illustrated) for turning on the first switch 55 of the first pushbutton switch 80, and the second switch 58 of the second pushbutton switch 90, by pressing and displacing the operation portions 55*s*, 58*s*. The stroke L2 can be, for example, 1 mm or less.

The two-stage pushbutton switch device 50 described above can pressing operate (presses and displaces) the pushbutton 51 to, while deflecting (compressing) the load absorption spring 52 and the intermediate spring 57 of the second pushbutton switch 90, transmit the displacement to the first pressing member 53 of the first pushbutton switch 80, the first switch 55, and the second pressing member 56 of the second pushbutton switch 90, and sequentially turn on the first switch 55 and the second switch 58. One example of control is now described. A pressing force (energizing force) applied to the pushbutton 51 by a finger of a user (energizing means) is transmitted to the load absorption spring 52. As a movement amount of the finger (energizing force) increases, the load absorption spring 52 is compressed and the elastic force of the load absorption spring 52 increases. The pressing portion 53*a* of the first pressing member 53 of the first pushbutton switch 80 pushes the operation portion 55*s* by the elastic force of the load absorption spring 52, and when the elastic force of the load absorption spring 52 exceeds an operation force amount of the first switch 55, the first switch 55 is turned on. When the pushbutton 51 is pressed further, the intermediate spring 57 is pressed via the load absorption spring 52, the first pressing member 53 of the first pushbutton switch 80, the first switch 55, and the second pressing member 56 of the second pushbutton switch 90, the first pressing member 53, the first switch 55, and the second pressing member 56 move while compressing the intermediate spring 57, the pressing portion 56*a* contacts with and presses the operation portion 58*s*, and the second switch 58 is turned on. After the second switch 58 is turned on, the pushbutton 51 abuts to the pressing position stopper 60, and the pressing position is regulated.

Thus, even when further pressing force is applied to the pushbutton 51, the loads to the second switch 58 and the first switch 55 are not increased. In this embodiment, the stroke L2 is set to be smaller than the stroke L. Thus, a movement amount of the first switch 55 of the first pushbutton switch 80 is small, and a trouble such as damaging in wiring is hard to occur. There is a degree of freedom in setting of the stroke L until the pushbutton 51 abuts to the pressing position stopper 60, and the stroke L2 until the second pressing member 56 of the second pushbutton switch 90 turns on the second switch 58. Similar operation feeling as that of conventional devices that perform air supply and water supply (spraying) can be acquired by changing a press displacement position of the piston body slidably fit in the cylinder.

The first embodiment of FIG. 5A is an embodiment in which the load absorption spring 52 is inserted to between the pushbutton 51 and the first pushbutton switch 80 (the first switch 55 thereof). FIG. 5B and FIG. 5C are modifications of the first embodiment, in which the insertion positions of the load absorption spring 52 are different from the insertion position of the first embodiment. That is, in FIG. 5B, the load absorption spring 52 is inserted to between the first pushbutton switch 80 (the first switch 55 thereof) and the second pushbutton switch 90 (the second pressing member 56 thereof), and in FIG. 5C, the load absorption spring 52 is inserted to between the second pushbutton switch 90 (the second switch 58 thereof) and the reaction force wall 59. In the embodiments of FIG. 5B and FIG. 5C, similar action and effect as those of the embodiment of FIG. 5A can be acquired. The load absorption spring 52 may be inserted to any one or more of between the pushbutton 51 and the first pushbutton switch 80 (the first pressing member 53 thereof) (FIG. 5A), between the first pushbutton switch 80 (the first switch 55 thereof) and the second pushbutton switch 90 (the second pressing member 56 thereof) (FIG. 5B), and between the second pushbutton switch 90 (the second switch 58 thereof) and the reaction force wall 59 (FIG. 5C). In the examples of FIG. 5A and FIG. 5B, the intermediate spring 57 composes the energizing means that energizes the reaction force wall 59. In the example of FIG. 5C, the load absorption spring 52 composes the energizing means that energizes the reaction force wall 59.

Figure 6A:
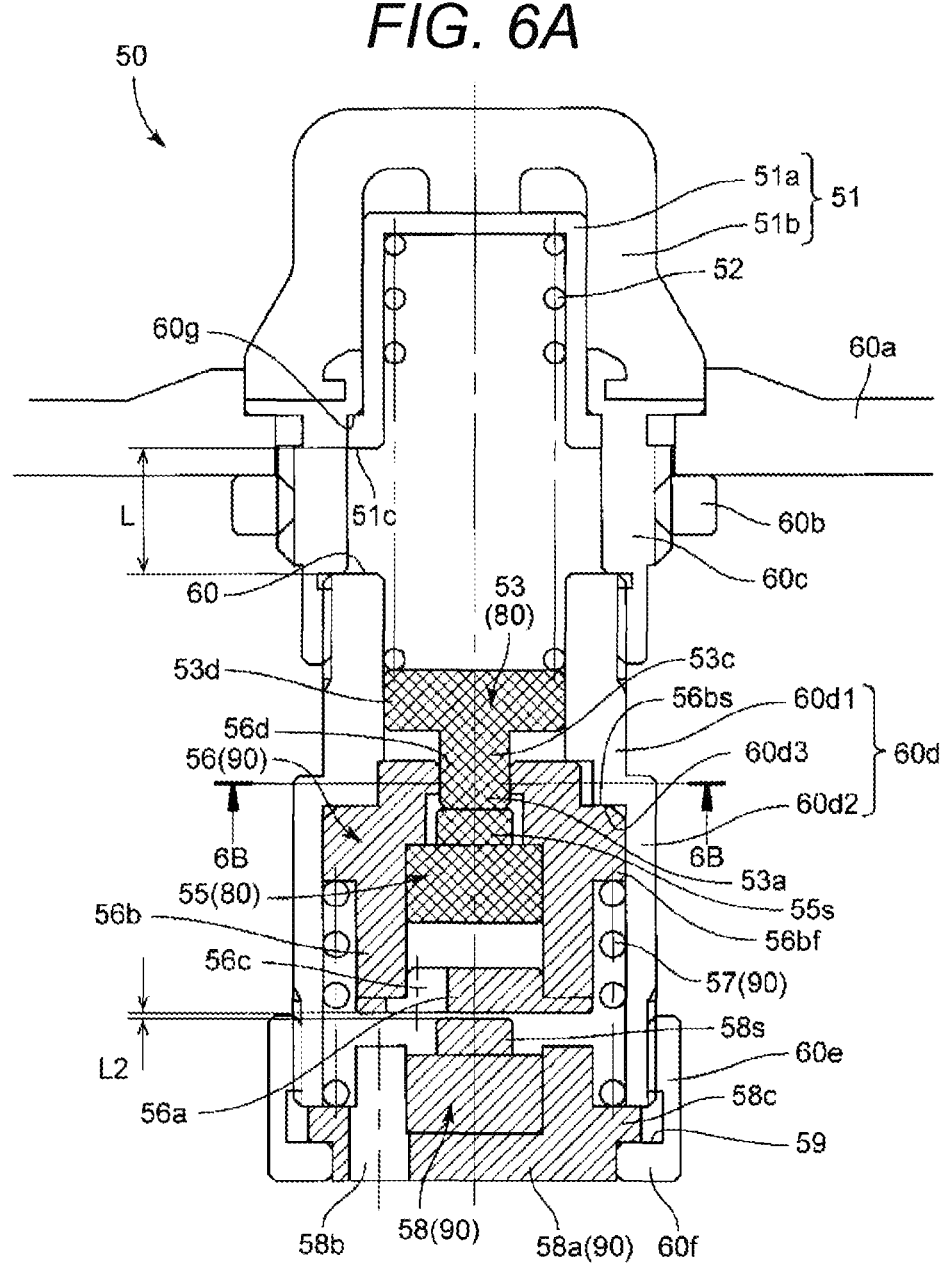
FIG. 6A and FIG. 6B illustrate a first embodiment in which the two-stage pushbutton switch device of FIG. 5A is illustrated more particularly.
Figure 6B:
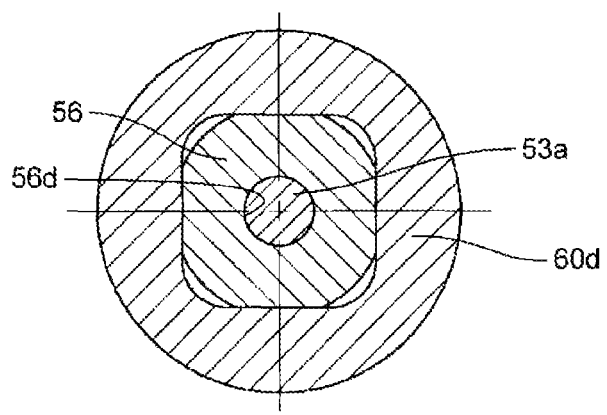
Figure 7:
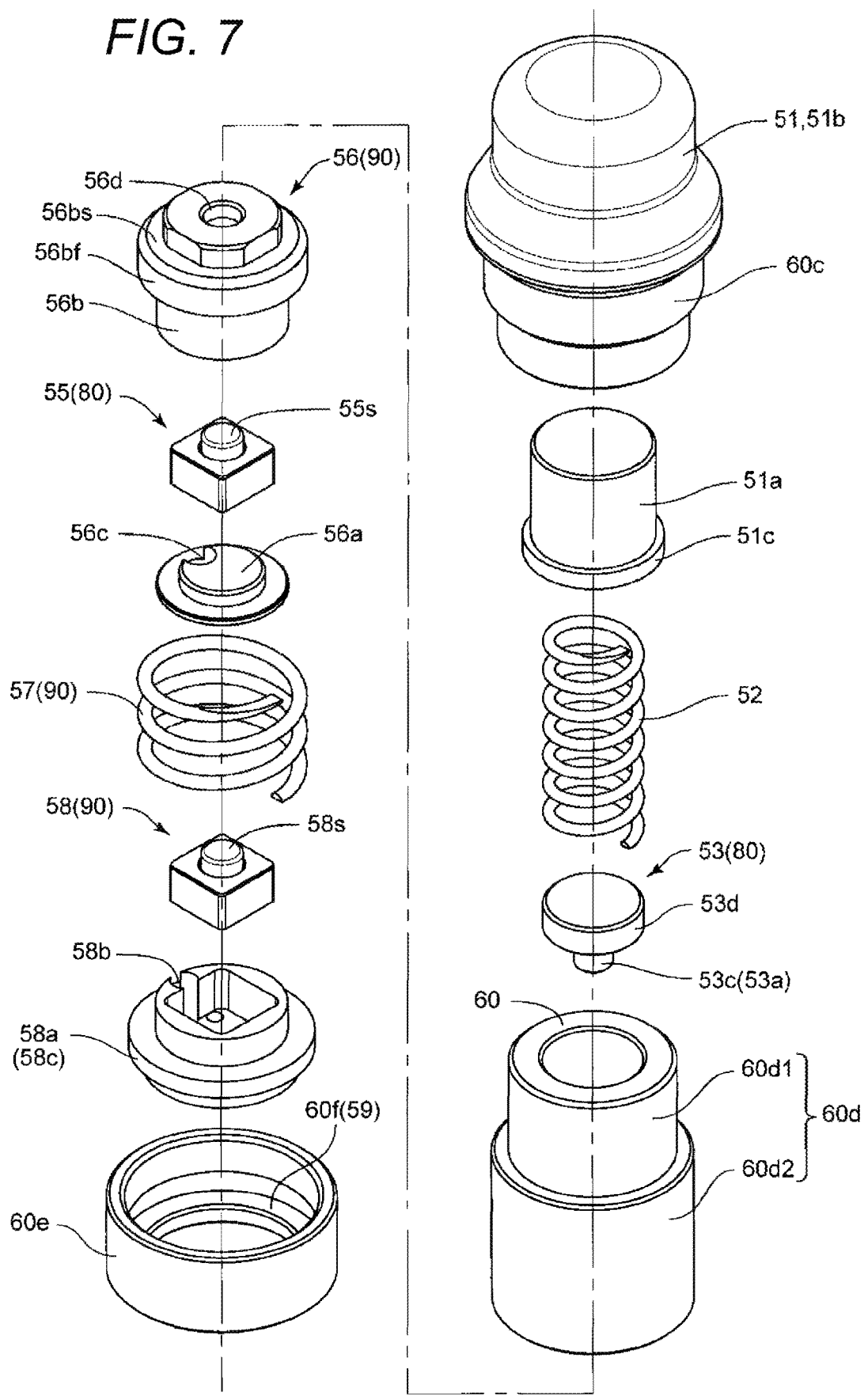
FIG. 7 is an exploded perspective view of the first embodiment of the two-stage pushbutton switch device of FIG. 6.

FIG. 6A, FIG. 6B, and FIG. 7 are embodiments in which the embodiment of FIG. 5A is more particularly made. In this embodiment, a housing wall 60*a*, a first cylinder 60*c* fixed to the housing wall 60*a* with a slip prevention ring 60*b*, a second cylinder 60*d* screwed and fixed to the first cylinder 60*c*, and an end portion cap 60*e* screwed and fixed to the second cylinder 60*d* are included as fixation members. An end portion flange 60*f* of this end portion cap 60*e* composes the reaction force wall 59 of the embodiment of FIG. 5, and an upper end surface of the second cylinder 60*d* composes the pressing position stopper 60. The second cylinder 60*d* has a small diameter portion 60*d*1 in an upper portion of the drawing, and a large diameter portion 60*d*2 in a lower portion of the drawing, and includes a projection position stopper 60*d*3 that regulates a projection position of the first switch 55, in an inner step portion between the small diameter portion 60*d*1 and the large diameter portion 60*d*2.

The pushbutton 51 is composed of a hat-shape button 51*a* having a hat-shape cross section, and a rubber button cover 51*b* covering the hat-shape button 51*a*. A projection end of the pushbutton 51 is regulated in a position in which the stopper flange 51*c* of a lower end portion of the drawing of the hat-shape button 51*a* abuts to an inner flange portion 60*g* of the first cylinder 60*c*. A stroke from a projection position (initial position state) of the pushbutton 51 to a pressing position in which the stopper flange 51*c* abuts to the pressing position stopper 60 is L.

An outer flange 53*d* of the first pressing member 53 of the first pushbutton switch 80 is slidably fit to the small diameter portion 60*d*1 of the second cylinder 60*d*. A cylindrical portion 56*b* (upper end flange 56*bf*) of the second pressing member 56 to which the first switch 55 is adhered and fixed, is slidably fit to the large diameter portion 60*d*2. The load absorption spring 52 is inserted to between the hat-shape button 51*a* and the first pressing member 53, in a compressed state. A stopper 56*bs* of an upper end portion of the upper end flange 56*bf* abuts to a projection position stopper 60*d*3 of the second cylinder 60*d* to regulate a projection position of the second pressing member 56. An axis portion through hole 56*d* is drilled and provided in an upper end portion of the cylindrical portion 56*b* of the second pressing member 56, and a pressing portion 53*a* of a lower end portion of a central axis 53*c* of the first pressing member 53 is slidably fit to the axis portion through hole 56*d*. A lower end portion of the pressing portion 53*a* and the operation portion 55*s* of the first switch 55 face (contact) with each other. A pressing portion 56*a* is adhered and fixed to a lower end portion of the cylindrical portion 56*b*, and a wiring hole 56*c* through which wiring of the first switch 55 passes is formed in the pressing portion 56*a*.

The second switch 58 of the second pushbutton switch 90 is adhered and fixed to the cylindrical second switch holder 58a, and a wiring hole 58b through which wiring of the first switch 55 and wiring of the second switch 58 pass is formed in the second switch holder 58a. The intermediate spring 57 is inserted to between the upper end flange 56bf of the cylindrical portion 56b, and the outer flange 58c of the second switch holder 58a, in a compressed state. The intermediate spring 57 maintains the second pressing member 56 (the first switch 55) to the projection position (initial position) in which the stopper 56bs abuts to the first projection position stopper 60d3, by the initial elastic force. That is, the first projection position stopper 60d3 sets an initial elastic force of the intermediate spring 57. For example, the initial elastic force of the intermediate spring 57 can be set to be larger for 1N or more than the pressing force of when the first switch 55 that is in the first stage is operated. The outer flange 58c is pushed in a lower end portion of the second cylinder 60d by the end portion flange 60f (the reaction force wall 59) of the end portion cap 60e, and thereby, the second switch holder 58a is fixed. The second switch holder 58a can be screwed or adhered and fixed to the second cylinder 60d. A gap (stroke) L2 is set in between a lower end portion of the pressing portion (pressing member) 56a, and an operation portion 58s of the second switch 58.

In the embodiments of FIG. 6 and FIG. 7, an initial elastic force and a spring constant of the intermediate spring 57 are larger than those of the load absorption spring 52, and the line diameters are thick in the order. Since the initial position of the projection direction of the second pressing member 56 is regulated, the initial elastic force of the intermediate spring 57 can be set to be larger than the load absorption spring 52. The initial elastic force can be set not only by the spring constant of the intermediate spring 57, but also by an equilibrium length and an initial compression length of the intermediate spring 57.

Figure 8:
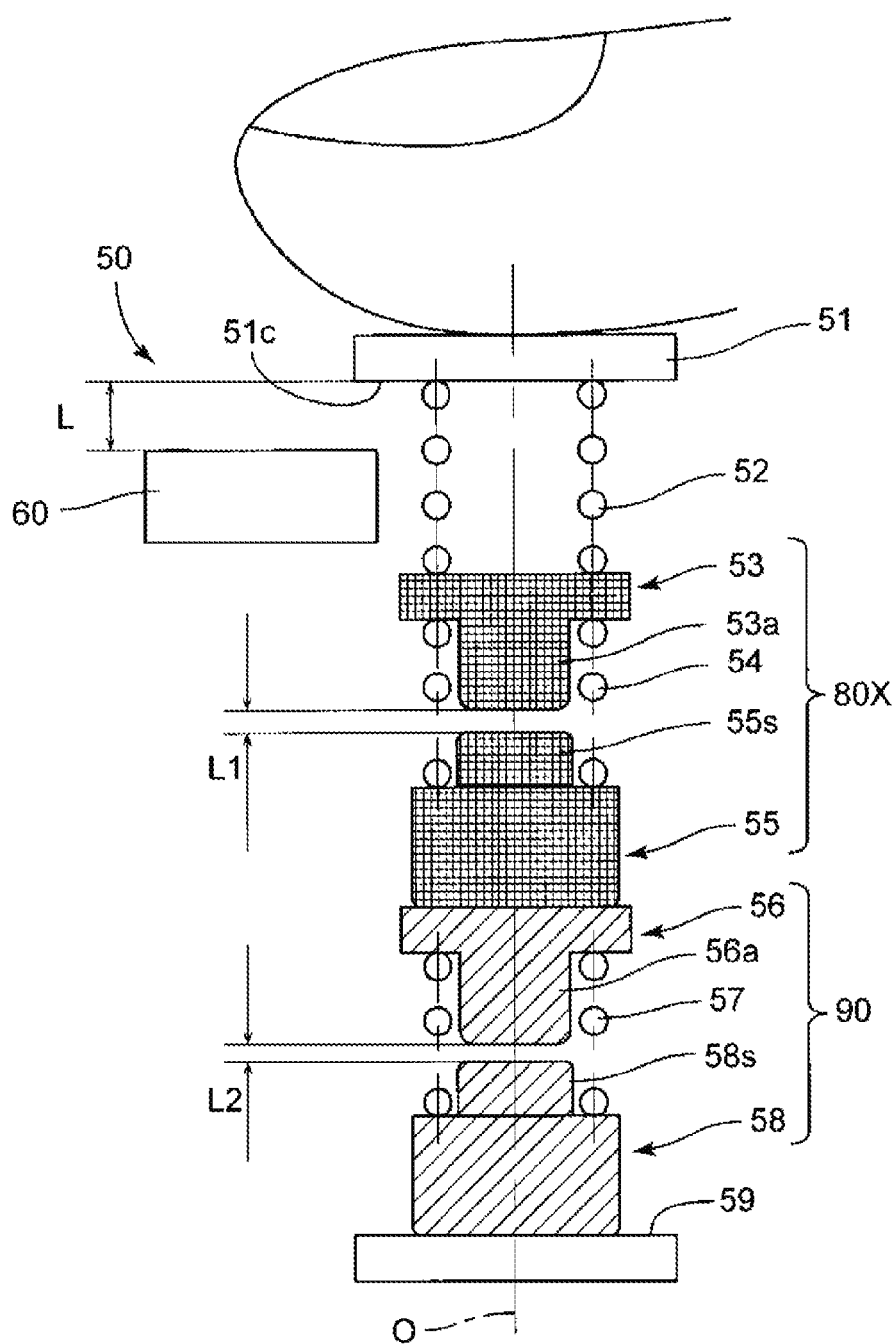
FIG. 8 is a conceptual diagram illustrating one embodiment of a second embodiment group of the two-stage pushbutton switch device according to the present disclosure.

Next, FIG. 8 is a conceptual diagram of a second embodiment in which the present disclosure is applied to the two-stage pushbutton switch device 50. In this second embodiment, an intermediate spring (an intermediate spring member) 54 is inserted to between the first pressing member 53 and the first switch 55 of the first embodiment and modification illustrated in FIG. 5 (FIG. 5A, FIG. 5B, and FIG. 5C), and thereby, a first pushbutton switch 80X is configured. That is, in the first embodiment and modification thereof, the first pushbutton switch 80X is configured by inserting the intermediate spring 54 to between the first pressing member 53 and the first switch 55 of the first pushbutton switch 80, and applying a separation force to the first pressing member 53 and the first switch 55. The configurations of the first pushbutton switch 80X and the second pushbutton switch 90 are substantially the same. Hatching of the same manner is applied to main elements composing the first pushbutton switch 80X, and hatching of the same manner that is different from the first pushbutton switch 80X is applied to main elements composing the second pushbutton switch 90, so that discrimination of units is facilitated.

In this two-stage pushbutton switch device 50 of FIG. 8, the pressing portion 53a of the first pressing member 53 and the operation portion 55s of the first switch 55 are normally separated for a gap (stroke L1) by the intermediate spring 54 of the first pushbutton switch 80X. In the illustrated example, a stroke until the pushbutton 51 in an initial position (projection) state abuts to the pressing position stopper 60 is set as L, a stroke until the second pressing member 56 of the second pushbutton switch 90 turns on the second switch 58 is set as L2, and L, L1, and L2 are set to be L>L1>L2. Strictly, the strokes L, L1, L2 include a stroke (not illustrated) for turning on the first switch 55 of the first pushbutton switch 80X, and the second switch 58 of the second pushbutton switch 90, by pressing and displacing the operation portions 55s, 58s. Hereinafter, as similar to this, each of the strokes L, L1, L2 includes a stroke for turning on the first switch 55 and the second switch 58. The stroke L2 can be, for example, 1 mm or less.

In this second embodiment, the pressing force and the stroke can be increased by the intermediate spring 54 of the first pushbutton switch 80X. A stroke for the operation of the second switch 58 can be borne by the load absorption spring 52 by making the initial elastic force of the intermediate spring 57 of the second pushbutton switch 90 to be longer. An order of operation of the first switch 55 and the second switch 58 can be reversed by setting the initial elastic force (spring constant) of the intermediate spring 57 of the second pushbutton switch 90 to be smaller than the initial elastic force (spring constant) of the intermediate spring 54 of the first pushbutton switch 80X.

Figure 9A:
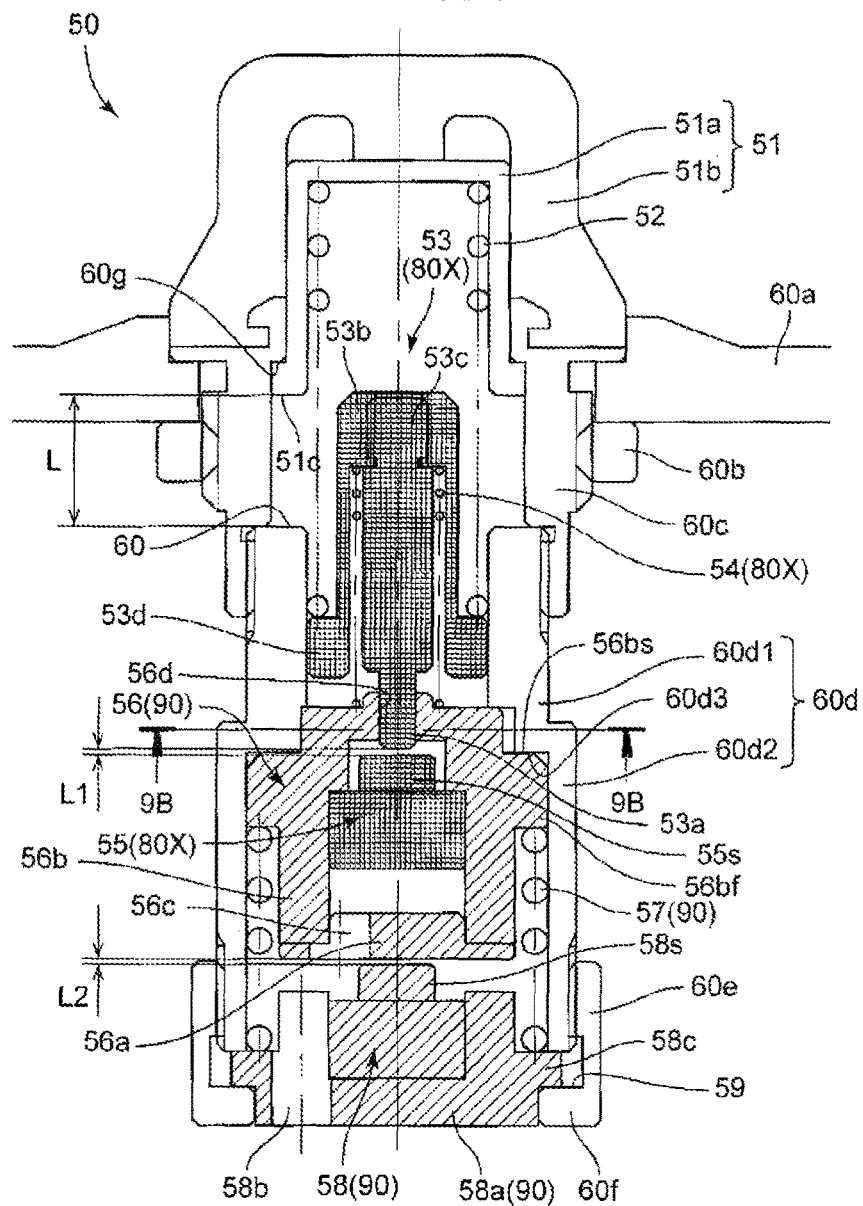
FIG. 9A and FIG. 9B illustrate a second embodiment in which the two-stage pushbutton switch device of FIG. 8 is illustrated more particularly.
Figure 9B:
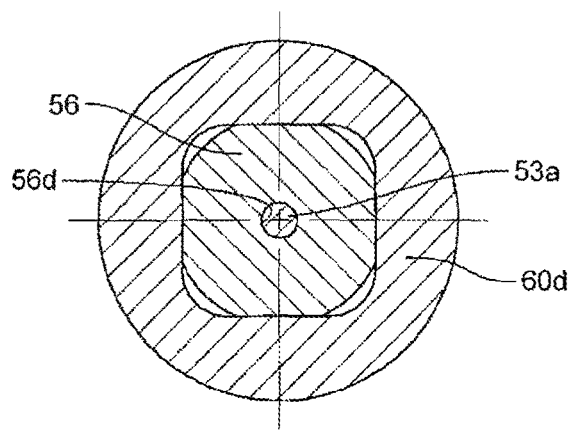
Figure 10:
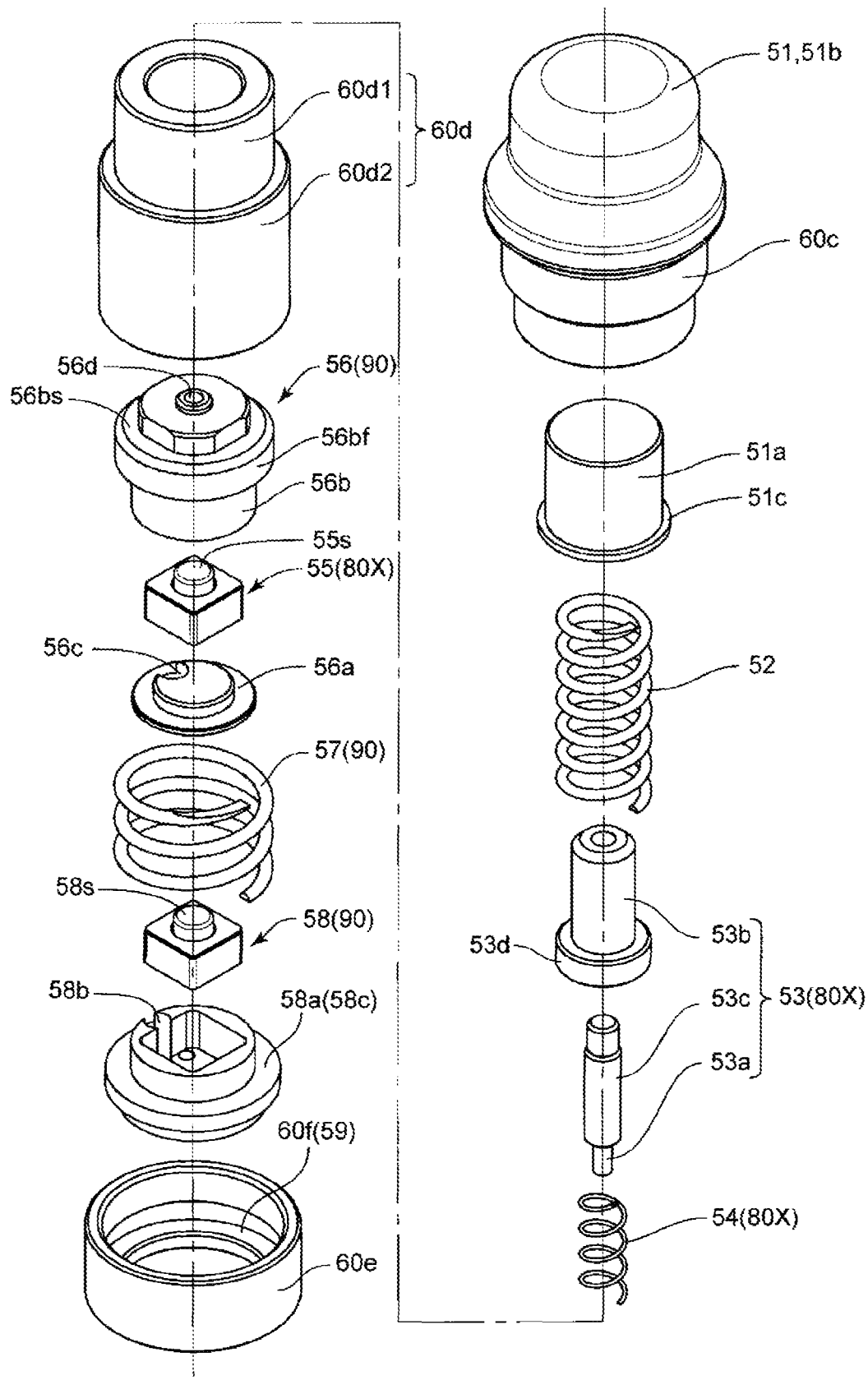
FIG. 10 is an exploded perspective view of the two-stage pushbutton switch device of FIG. 9.

FIG. 9 and FIG. 10 are embodiments in which the second embodiment of FIG. 8 is more particularly made. A main difference between the embodiment of FIG. 9 and FIG. 10 and the embodiment of FIG. 6 and FIG. 7 is presence of the intermediate spring 54 of the first pushbutton switch 80X. In the drawings, common portions are added with common numerals.

The first pressing member 53 of the first pushbutton switch 80X is composed of an outer cylinder portion 53b, and a central axis 53c screwed and fixed to an axis hole of the outer cylinder portion 53b. The load absorption spring 52 is inserted to between the outer flange 53d formed in a lower end portion of the drawing of the outer cylinder portion 53b, and the hat-shape button 51a, in a compressed state. The outer flange 53d is slidably fit to the small diameter portion 60d1 of the second cylinder 60d. An axis portion through hole 56d is drilled and provided in an upper end portion of the cylindrical portion 56b, and a pressing portion 53a of a lower end portion of a central axis 53c of the first pressing member 53 is slidably fit to the axis portion through hole 56d. A gap (stroke) L1 is set in between a lower end portion of the pressing portion 53a, and an operation portion 55s of the first switch 55. The intermediate spring 54 is inserted to an annular gap between the central axis 53c and the outer cylinder portion 53b of the first pressing member 53 in a compressed state, and presses and energizes the second pressing member 56 (the first switch 55) downward. The first pressing member 53 of the first pushbutton switch 80X is maintained to be in the initial position in which the elastic forces of the load absorption spring 52 and the intermediate spring 54 are equal.

In the embodiment of FIG. 9 and FIG. 10, the initial elastic force of the intermediate spring 57 of the second pushbutton switch 90 is the largest, and the initial elastic forces of the load absorption spring 52 and the intermediate spring 54 of the first pushbutton switch 80X are the same. The spring constant is large in order of the intermediate spring 54 of the first pushbutton switch 80X, and the load absorption spring 52 and the intermediate spring 57 of the second pushbutton switch 90, and the line diameters are thick in the order. In the embodiment of FIG. 9, since the initial elastic forces of the load absorption spring 52 and the intermediate spring 54 are the same, movement regulation of the first pressing member 53 (the intermediate spring 54) is not necessary.

Figure 11:
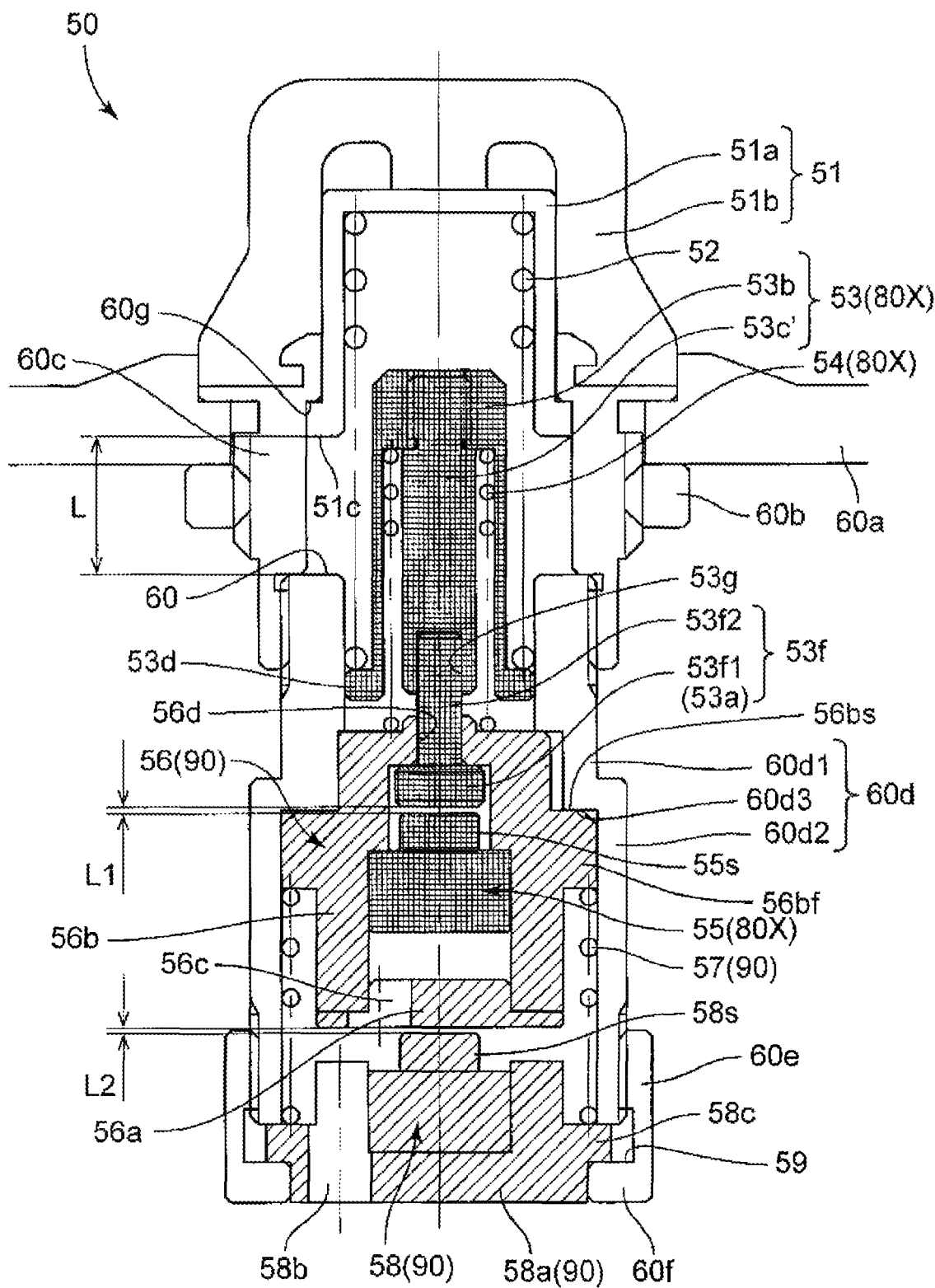
FIG. 11 is a vertical cross sectional view illustrating another embodiment of the second embodiment of FIG. 9, in which the two-stage pushbutton switch device according to the present disclosure is illustrated more particularly.

On the other hand, the embodiment of FIG. 11 is an embodiment of another aspect of the second embodiment illustrated in FIG. 9A, that is suitable for when the initial elastic force (initial deflection amount) of the intermediate spring 54 of the first pushbutton switch 80X is set to be large. In this embodiment, a form of the first pressing member 53 of the first pushbutton switch 80X is different from the first pressing member 53 of the embodiment of FIG. 9 and FIG. 10. While the first pressing member 53 is composed of the outer cylinder portion 53b and the central axis 53c in the embodiment of FIG. 9 and FIG. 10, the first pressing member 53 is composed of the outer cylinder portion 53b, a central axis 53c', and a slip prevention pin 53f in the embodiment of FIG. 11. A coupling hole 53g opened in a lower end of an axis portion is drilled and provided in the central axis 53c'. The slip prevention pin 53f includes a head portion 53f1, and an insertion axis portion 53f2 that is inserted to the coupling hole 53g. In assembly of the first pressing member 53, the intermediate spring 54 that has been compressed is inserted to between the outer cylinder portion 53b of the first pressing member 53 and the central axis 53c'. In the insertion state the insertion axis portion 53f2 of the slip prevention pin 53f is inserted from the axis portion through hole 56d of the cylindrical portion 56b, is further inserted to the coupling hole 53g of the central axis 53c', and is adhered (or press fit) and fixed. Elongation (an initial elastic force) of the intermediate spring 54 is regulated by the outer cylinder portion 53b, the central axis 53c', and the slip prevention pin 53f. That is, the initial elastic force of the intermediate spring 54 is set by the outer cylinder portion 53b, the central axis 53c', and the slip prevention pin 53f. A lower end portion of the head portion 53f1 composes the pressing portion 53a. The gap (stroke) L1 is formed in between the head portion 53f1 (the pressing portion 53a) and an operation portion 55s of the first switch 55. Other components are common with the embodiment of FIG. 9 and FIG. 10. Common portions are added with common numerals.

The two-stage pushbutton switch device 50 of FIG. 11 can pressing operate the pushbutton 51 of the first pushbutton switch 80X to, while deflecting (compressing) the load absorption spring 52, the intermediate spring 54 of the first pushbutton switch 80X, and the intermediate spring 57 of the second pushbutton switch 90, transmit the displacement to the first pressing member 53 of the first pushbutton switch 80X, the first switch 55, and the second pressing member 56 of the second pushbutton switch 90, and sequentially turn on the first switch 55 and the second switch 58. One example of control is now described. A pressing force applied to the pushbutton 51 by a finger of a user is transmitted to the load absorption spring 52. As a movement amount of the finger increases, the load absorption spring 52 is compressed and the elastic force of the load absorption spring 52 increases. Then, when the first pressing member 53 of the first pushbutton switch 80X is pressed by the elastic force of the load absorption spring 52, and the pressing force exceeds the initial elastic force of the intermediate spring 54, the first pressing member 53 descends while compressing the intermediate spring 54, the pressing portion 53a presses the operation portion 55s, and the first switch 55 is turned on when the pressing force exceeds the operation force amount of the first switch 55. When the pushbutton 51 is pressed further, the intermediate spring 57 is pressed via the load absorption spring 52, the first pressing member 53 and the first switch 55 of the first pushbutton switch 80X, and the second pressing member 56 of the second pushbutton switch 90, and the pressing force exceeds the initial elastic force of the intermediate spring 57, the first pressing member 53, the first switch 55, and the second pressing member 56 move while compressing the intermediate spring 57, the pressing portion 56a contacts with and presses the operation portion 58s, and the second switch 58 is turned on. After the second switch 58 is turned on, the pushbutton 51 (the stopper flange 51c) abuts to the pressing position stopper 60, and the pressing position is regulated.

According to the embodiment of FIG. 11, even when the force of the intermediate spring 54 of the first pushbutton switch 80X is large, the intermediate spring 54 is inserted and supported to between the first pressing member 53 and the first switch 55 in a compressed state. An order of operation of the first switch 55 and the second switch 58 can be reversed by setting the initial elastic force (spring constant) of the intermediate spring 57 of the second pushbutton switch 90 to be smaller than the initial elastic force (spring constant) of the intermediate spring 54 of the first pushbutton switch 80X.

Figure 12:
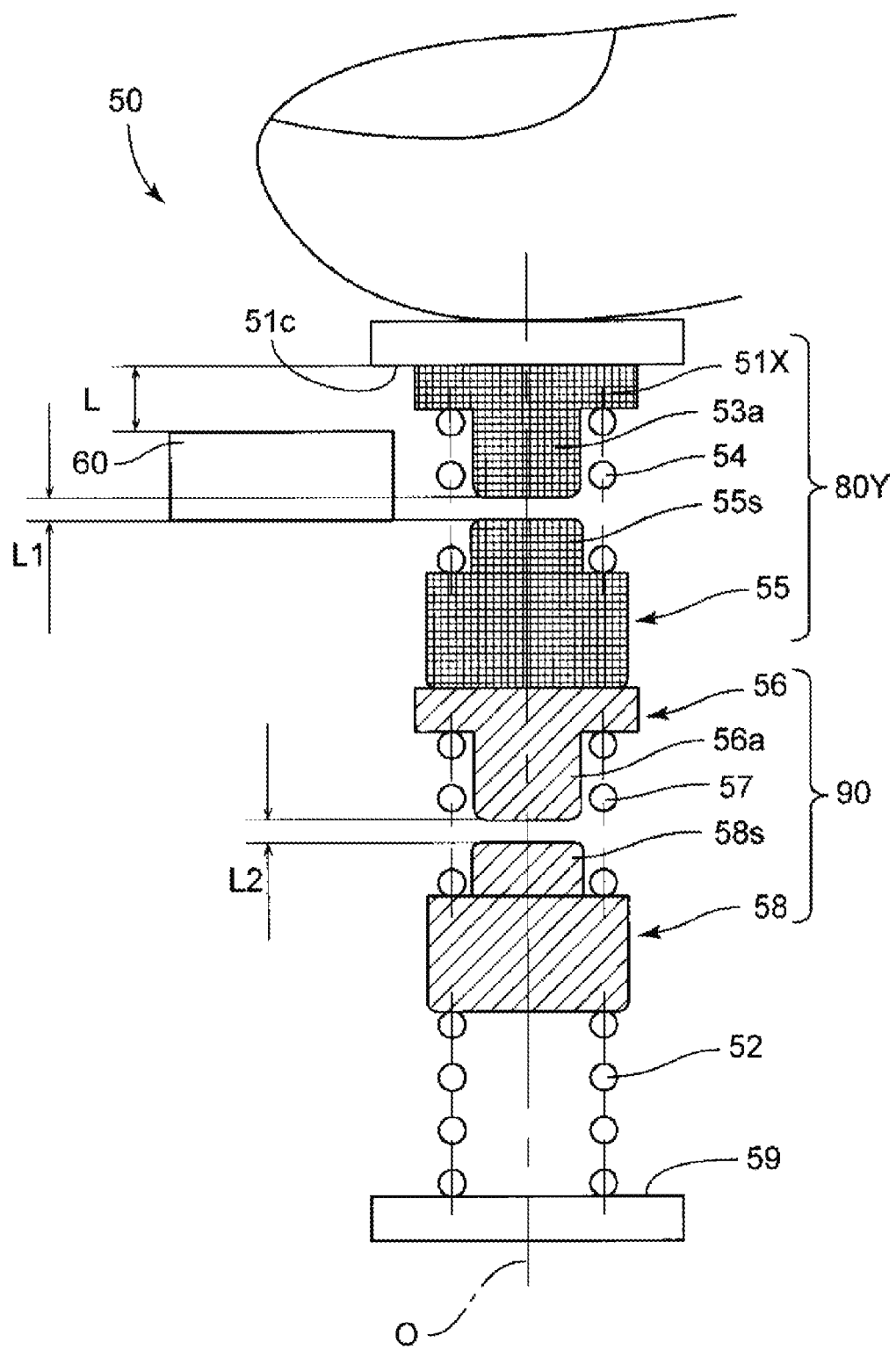
FIG. 12 is a conceptual diagram illustrating a modification of the second embodiment group of the two-stage pushbutton switch device according to the present disclosure.

FIG. 12 is a conceptual diagram of a modification of the second embodiment (FIG. 8) of a two-stage pushbutton switch structure according to the present disclosure. This embodiment (modification) corresponds to an embodiment in which an arrangement position of the load absorption spring 52 in the second embodiment is changed to between the reaction force wall 59 and the second pushbutton switch 90, and the pushbutton 51 and the first pressing member 53 are made integrally to be changed to a pushbutton 51X. That is, in this embodiment, a first pushbutton switch 80Y including the pushbutton 51X, the second pushbutton switch 90, and the load absorption spring 52 are located in the same axial line O, in order from the pushbutton 51X side. A lower end portion of the load absorption spring 52 abuts (is fixed) to the reaction force wall 59. The first pushbutton switch 80Y is composed of the pushbutton 51X, the intermediate spring 54, and the first switch 55. The second pushbutton switch 90 is composed of the second pressing member 56, the intermediate spring 57, and the second switch 58. Hatching of the same manner is applied to main elements composing the first pushbutton switch 80Y, and hatching of the same manner that is different from the first pushbutton switch 80Y is applied to main elements composing the second pushbutton switch 90, so that discrimination of units is facilitated.

In this embodiment, not only the first switch 55 of the first pushbutton switch 80Y and the second pressing member 56 of the second pushbutton switch 90 are sandwiched between the intermediate spring 54 and the intermediate spring 57 and are movable, but also the second switch 58 of the second pushbutton switch 90 is sandwiched between the intermediate spring 57 and the load absorption spring 52 and is movable.

The pushbutton 51X has the stopper flange 51c that abuts to the pressing position stopper 60, and the pressing portion 53a that faces to the operation portion 55s of the first switch 55 of the first pushbutton switch 80Y. In this embodiment, when the pushbutton 51X is pressed, while all springs of the intermediate spring 54 of the first pushbutton switch 80Y, the intermediate spring 57 of the second pushbutton switch 90, and the load absorption spring 52 are deflected (compressed), the first switch 55 and the second switch 58 are sequentially turned on. The spring forces of the intermediate spring 54, the intermediate spring 57, and the load absorption spring 52 are set so that the last switch (the first switch 55 or the second switch 58) is turned on before the stopper flange 51c of the pushbutton 51X abuts to the pressing position stopper 60. Which of the first switch 55 and the second switch 58 is turned on first can be determined by setting of the spring forces of the intermediate spring 54 of the first pushbutton switch 80Y, the intermediate spring 57 of the second pushbutton switch 90, and the load absorption spring 52.

Figure 13:
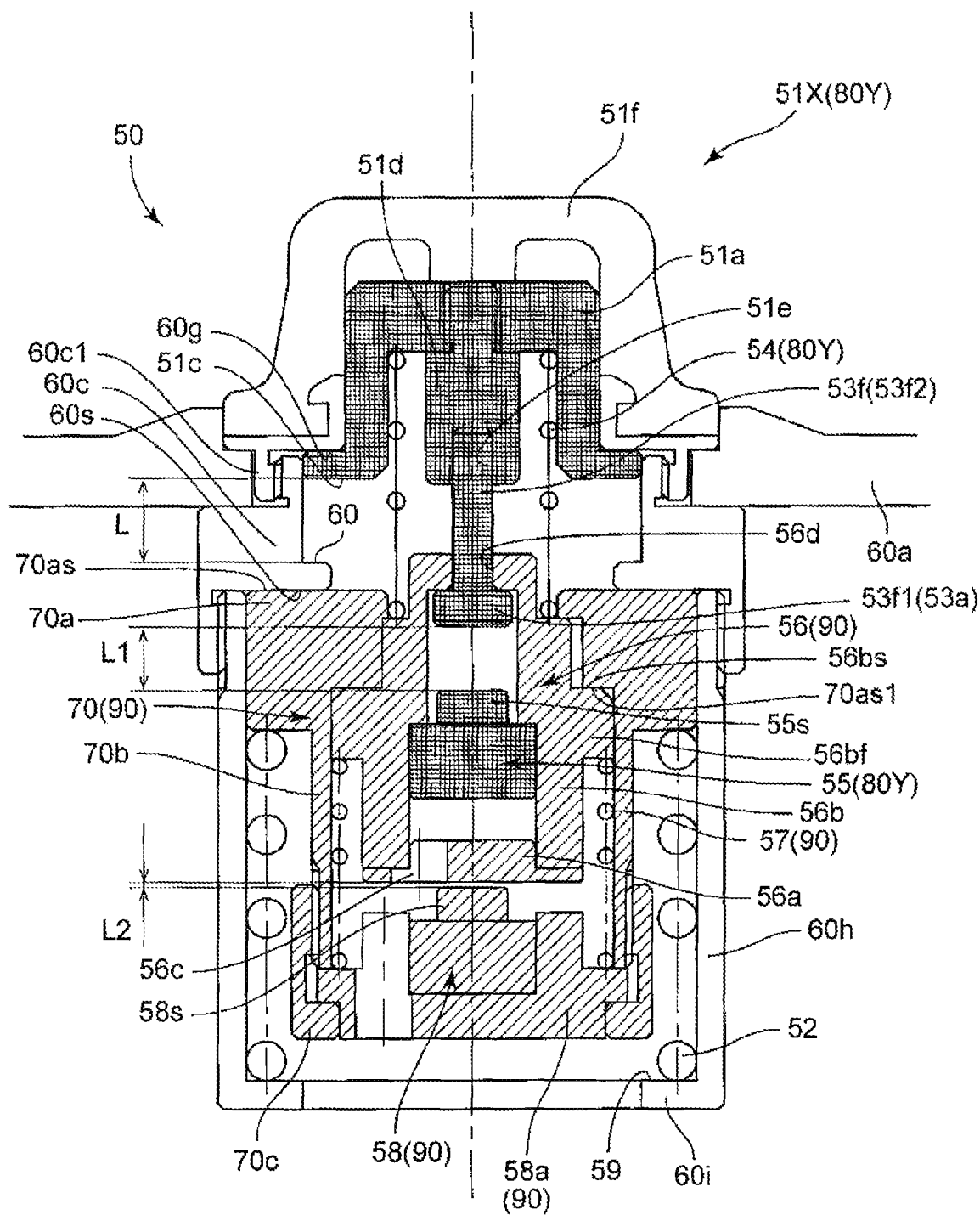
FIG. 13 is a vertical cross sectional view illustrating an embodiment in which the two-stage pushbutton switch device of FIG. 12 is illustrated more particularly.

FIG. 13 is an embodiment in which the modification of the second embodiment of FIG. 12 is more particularly made. The rubber button cover 51f and the first cylinder 60c are fixed to the housing wall 60a via a dividing ring 60c1. A fixed cylinder 60h fit with the outer cylinder body 70 is screwed and fixed to the first cylinder 60c.

The outer cylinder body 70 has a cylindrical body 70b having a flange 70a that slides with a fixed cylinder 60h, in an upper end portion, and a cap member 70c screwed and fixed to a lower end portion of the cylindrical body 70b. The second switch 58 (the second switch holder 58a) is fixed to between the lower end portion of the cylindrical body 70b and the cap member 70c. That is, the second switch 58 moves together with the outer cylinder body 70. The load absorption spring 52 is inserted to an annular space between the fixed cylinder 60h and the outer cylinder body 70, in a compressed state. The outer cylinder body 70 is energized to a projection direction by the elastic force of the load absorption spring 52, a stopper 70as of an upper surface of the flange 70a abuts to a stopper 60s of a lower surface of the first cylinder 60c, the projection direction is regulated, and the initial elastic force of the load absorption spring 52 is set.

The second pressing member 56 having the first switch 55 of the first pushbutton switch 80Y is slidably fit to the cylindrical body 70b of the outer cylinder body 70. The configuration of the second pressing member 56 of the second pushbutton switch 90 is similar to that of the embodiment of FIG. 8. The first switch 55 is adhered and fixed to the cylindrical portion 56b, and the cylindrical portion 56b is slidably supported to the cylindrical body 70b. A stopper 56bs abuts to an inner peripheral lower surface stopper 70as1 of the flange 70a of the outer cylinder body 70 to regulate the projection position of the second pressing member 56. A pressing portion (pressing member) 56a is adhered and fixed to a lower end portion of the cylindrical portion 56b of the second pressing member 56, and a wiring hole 56c through which wiring of the first switch 55 passes is formed in the pressing portion 56a. The axis portion through hole 56d is drilled and provided in an upper end portion of the cylindrical portion 56b. The intermediate spring 57 in a compressed state is accommodated in between the upper end flange 56bf of the second pressing member 56 of the second pushbutton switch 90, and the second switch holder 58a.

The pushbutton 51X has the hat-shape button 51a located in the rubber button cover 51f. The intermediate spring 54 of the first pushbutton switch 80Y is inserted to between the hat-shape button 51a and the upper end surface of the second pressing member 56. A coupling rod 51d is screwed and fixed to an axis portion of the hat-shape button 51a. The insertion axis portion 53f2 of the slip prevention pin 53f that has been inserted from the cylindrical portion 56b into the axis hole 51e of the coupling rod 51d through the axis portion through hole 56d, is press fit and fixed. In assembly of the hat-shape button 51a and the second pressing member 56, the intermediate spring 54 that has been compressed is inserted to between the coupling rod 51d and the hat-shape button 51a. In the insertion state the insertion axis portion 53f2 of the slip prevention pin 53f is inserted from the axis portion through hole 56d of the cylindrical portion 56b, is further inserted to the axis hole 51e, and is adhered (or press fit) and fixed. A lower end portion of the head portion 53f1 of this slip prevention pin 53f composes the pressing portion 53a. The gap (stroke) L1 is formed in between the head portion 53f1 (the pressing portion 53a) and the operation portion 55s of the first switch 55. The intermediate spring 57 of the second pushbutton switch 90 maintains the second pressing member 56 (the first switch 55) to the projection position (initial position) in which the stopper 56bs abuts to the stopper 70as1 of the outer cylinder body 70, by the initial elastic force. That is, the stopper 70as1 sets the initial elastic force of the intermediate spring 57. Elongation (the initial elastic force) of the intermediate spring 54 of the first pushbutton switch 80Y is regulated by the hat-shape button 51a, the coupling rod 51d, and the slip prevention pin 53f. That is, the initial elastic force of the intermediate spring 54 is set by the hat-shape button 51a, the coupling rod 51d, and the slip prevention pin 53f. The maximum projection position of the hat-shape button 51a is regulated in a position in which the stopper flange 51c abuts to the inner flange portion 60g of the division first cylinder 60c1.

Accordingly, in the embodiment of FIG. 13, when the rubber button cover 51f is deflected and the hat-shape button 51a is pressed and displaced, first, the elastic force of the intermediate spring 54 of the first pushbutton switch 80Y exceeds the initial elastic force and flexes. The hat-shape button 51a, the coupling rod 51d, and the slip prevention pin 53f are integrally displaced downward (are pressed and displaced, descends), and flex when the elastic forces of the intermediate spring 57 of the second pushbutton switch 90 and the load absorption spring 52 exceed the initial elastic force, and the second pressing member 56 and the outer cylinder body 70 are displaced (are pressed and displaced and descends) downward. In the process, the first switch 55 and the second switch 58 are sequentially turned on. Which of the first switch 55 and the second switch 58 is turned on first can be determined by setting of the spring forces (spring constants and initial elastic forces) of the intermediate spring 54, the intermediate spring 57, and the load absorption spring 52. Before the pushbutton 51X is pressed by the maximum stroke, the last switch (the first switch 55 or the second switch 58) is turned on.

Figure 14:
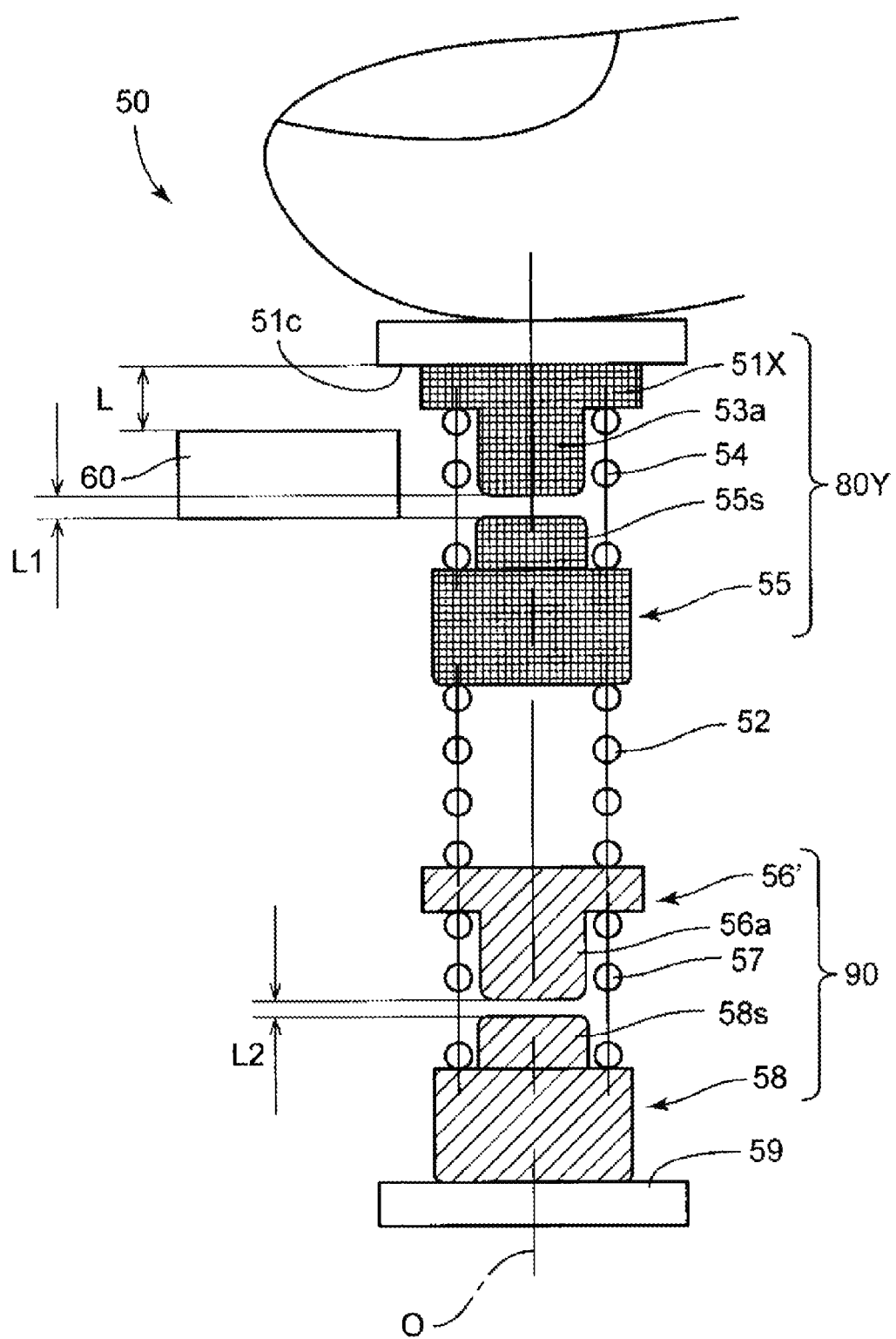
FIG. 14 is a conceptual diagram illustrating another modification of the second embodiment group of the two-stage pushbutton switch device according to the present disclosure.

FIG. 14 is another (a second) modification of the second embodiment (FIG. 8, FIG. 12) of the two-stage pushbutton switch structure according to the present disclosure. This second modification of the second embodiment corresponds to a modification in which an arrangement position of the load absorption spring 52 in the embodiment of FIG. 8 and FIG. 12 is changed to between the first pushbutton switch 80Y(80X) and the second pushbutton switch 90. That is, in the modification of FIG. 14, a first pushbutton switch 80Y including the pushbutton 51X, load absorption spring 52, and the second pushbutton switch 90 are arranged in the same axial line O, in order from the pushbutton 51X side. In an initial state (no-load state), a lower end portion of the second switch 58 of the pushbutton switch 90 abuts (is fixed) to the reaction force wall 59.

The first pushbutton switch 80Y is composed of the pushbutton 51X, the intermediate spring 54, and the first switch 55. The second pushbutton switch 90 is composed of the second pressing member 56', the intermediate spring 57, and the second switch 58. Hatching of the same manner is applied to main elements composing the first pushbutton switch 80Y, and hatching of the same manner that is different from the first pushbutton switch 80Y is applied to main elements composing the second pushbutton switch 90, so that discrimination of units is facilitated.

In the second modification of this second embodiment, the first switch 55 of the first pushbutton switch 80Y is sandwiched between the intermediate spring 54 and the load absorption spring 52, and is movable. A bottom portion of the second switch of the second pushbutton switch 90 abuts to the reaction force wall 59 and does not move (is fixed).

In the second modification of this second embodiment, in the initial state, movement is regulated so that the pushbutton 51X, the first switch 55, and the second pressing member 56' do not ascend (project) anymore, by the initial elastic force of the intermediate spring 54, the load absorption spring 52, and the intermediate spring 57. In this embodiment, the order of turning on of the first switch 55 and the second switch 58 can be set by setting of the spring constants and initial elastic forces of the intermediate spring 54, the load absorption spring 52, and the intermediate spring 57.

An example of control of when the second switch 58 and the first switch 55 are turned on in this order will be described. In a case of this control example, for the spring constants of the intermediate spring 54, the load absorption spring 52, and the intermediate spring 57, the intermediate spring 57 has the smallest spring constant, and the intermediate spring 54, and the load absorption spring 52 have larger spring constants in this order. The load absorption spring 52 has the largest initial elastic force, and the intermediate springs 57 and 54 have the equal initial elastic forces, or the intermediate spring 57 has smaller initial elastic force.

When the pushbutton 51X is imparted with a pressing force (energizing force) by a finger of a user, the force exceeds the initial elastic forces of the intermediate springs 54, 57, the pushbutton 51X is pressed and displaced (is displaced downward, descends) while compressing the intermediate springs 54, 57. Since the intermediate spring 57 has smaller spring constant than that of the intermediate spring 54, first, the second pressing member 56' (the pressing portion 56a thereof) approaches and abuts to the operation portion 58s of the second switch 58 to press the operation portion 58s. When the pressing of the pushbutton 51X continues and the pressing force to the operation portion 58s exceeds an operation force amount of the second switch 58, the second switch 58 is turned on. When the second switch 58 is turned on, since the second switch 58 is fixed, the press displacement (lower displacement, descending) of the second push member 56' anymore is regulated.

The pressing of the pushbutton 51X continues until the second switch 58 is turned on. Thus, the pushbutton 51X is pressed and displaced while compressing the intermediate spring 54, and the pressing portion 53a approaches the operation portion 55s. However, when the second switch 58 is turned on, the pressing portion 53a is apart from the operation portion 55s. The pressing portion 53a may abut with the operation portion 55s before the second switch 58 is turned on.

When the pushbutton 51X is further pressed after the second switch 58 is turned on, the pressing portion 53a abuts to and presses the operation portion 55s. When the pressing force to the operation portion 55s by the pressing portion 53a exceeds the operation force amount of the first switch 55, the first switch 55 is turned on.

When the pushbutton 51X is further pressed after the first switch 55 is turned on, the pushbutton 51X and the first switch 55 are integrally pressed down while compressing the load absorption spring 52, the stopper flange 51c abuts to the pressing position stopper 60, and further pressing of the pushbutton 51X is regulated. Thereby, even when the pushbutton 51X is strongly pressed, there is no fear that the first and second switches 55, 58 are damaged.

A gap to a position in which the stopper flange 51c of the pushbutton 51X abuts to the pressing position stopper 60 is set to be the stroke L, a gap between the pressing portion 53a and the operation portion 55s is set to be the stroke L1, and the gap between the pressing portion 53a and the operation portion 55s is set to be the stroke L2, in this example of control, L, L1, and L2 are set to be L>L1>L2.

According to the two-stage pushbutton switch structure of this embodiment, the movement amount of the first switch 55 can be easily reduced without moving the second switch 58 while the stroke of the pushbutton 51X is made longer. In this embodiment, the initial elastic force and the spring constant of the intermediate spring 57 are set to be the smallest (smaller than those of the intermediate spring 54), and the initial elastic force and the spring constant of the load absorption spring 52 are set to be the largest, so that the movement amount of the first switch 55 is small. The stroke L can be increased without changing the movement amount of the first switch 55, by adjusting the spring constant of the intermediate spring 54.

In this embodiment, the initial elastic forces of the intermediate spring 54, the load absorption spring 52, and the intermediate spring 57 can be adjusted by regulating (limiting a movable range) the projection movement (projection position, initial position) of the pushbutton 51X, the first switch 55 and the second pressing member 56', as similar to the embodiment described above.

When the spring constant and the initial elastic force of the intermediate spring 54 are set to be larger than those of the intermediate spring 57, the second switch 58 and the first switch 55 can be turned on in this order.

Figure 15:
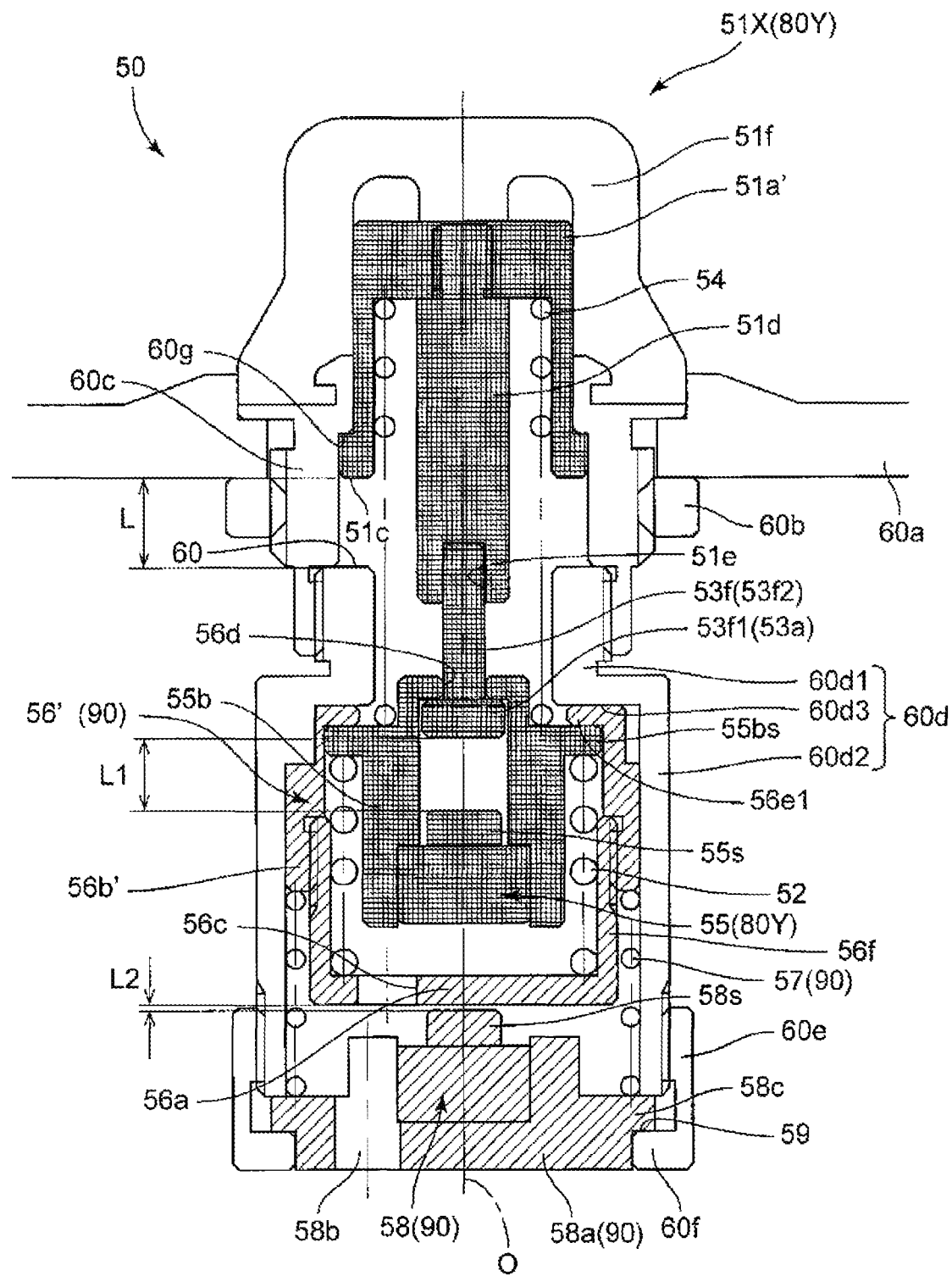
FIG. 15 is a vertical cross sectional view illustrating an embodiment in which the two-stage pushbutton switch device of FIG. 14 is illustrated more particularly.

FIG. 15 is an embodiment in which the second modification of the second embodiment of FIG. 14 is more particularly made. The first cylinder 60c fixed into the rubber button cover 51f is fixed to the housing wall 60a by the slip prevention ring 60b. The second cylinder 60d is screwed and fixed to the lower end portion of the first cylinder 60c. The second switch holder 58a is fixed to the lower end portion of the second cylinder 60d by the end portion cap 60e. The end portion flange 60f of this end portion cap 60e composes the reaction force wall 59 of the embodiment of FIG. 14, and the upper end surface of the second cylinder 60d composes the pressing position stopper 60.

The second cylinder 60d has a small diameter portion 60d1 in a upper portion of the drawing, and a large diameter portion 60d2 in a lower portion of the drawing, and includes the first projection position stopper 60d3 that regulates projection movement (a projection position and an initial position) of the first switch 55 (first switch holder 55b), in an inner step portion between the small diameter portion 60d1 and the large diameter portion 60d2.

In the second cylinder 60d, the second pressing member 56' (the cylindrical portion 56b') is slidably accommodated in the large diameter portion 60d2. The outer flange 58c of the second switch holder 58a is press pinched and fixed to between the lower end surface of the large diameter portion 60d2 and the end portion flange 60f of the end portion cap 60e.

The second pressing member 56' includes the cylindrical portion 56b' slidably fit to the large diameter portion 60d2 of the second cylinder 60d, and a bottomed cylindrical portion 56f screwed and fixed into a lower end portion of the cylindrical portion 56b'. The intermediate spring 57 is inserted to between the lower end surface of the cylindrical portion 56b', and an upper surface of the outer flange 58c of the second switch 58, in a compressed state. An upper surface of the inner flange 56e1 of an upper end portion abuts to a lower surface of the projection position stopper 60d3 by the elastic force of the intermediate spring 57, and thereby, projection movement (a relative projection position and an initial position) of the cylindrical portion 56b' is regulated. Abutment of the upper surface of the inner flange 56e1 and a lower surface of the projection position stopper 60d3 sets the initial elastic force of the intermediate spring 57.

The first switch holder 55b is slidably inserted into the cylindrical portion 56b' of the second pressing member 56', and the first switch 55 is fit and fixed to a lower end portion of the first switch holder 55b. In the first switch holder 55b, the outer stopper 55bs projected and formed in outward of a radial direction in an upper end portion is slidably fit to the cylindrical portion 56b'. The load absorption spring 52 is inserted to between the stopper 55bs and the pressing portion 56a formed by a bottom portion of the bottomed cylindrical portion 56f, in a compressed state. An upper surface of the stopper 55bs abuts to a lower surface of the inner flange 56e1 of an upper end portion of the cylindrical portion 56b' by the elastic force of the load absorption spring 52, and thereby, projection movement (a relative projection position and an initial position) of the first switch holder 55b is regulated. Abutment of the upper surface of the stopper 55bs and a lower surface of the inner flange 56e1 sets the initial elastic force of the load absorption spring 52.

The axis portion through hole 56d is formed in the upper end portion of the first switch holder 55b, and the slip prevention pin 53f (the insertion axis portion 53f2) is inserted through the axis portion through hole 56d from downward. The head portion 53f (the pressing portion 53a) for slip prevention and pressing of the operation portion 55s, that is located in the first switch holder 55b is formed in a lower end portion of the slip prevention pin 53f (the insertion axis portion 53f2). An upper end portion of the slip prevention pin 53f (the insertion axis portion 53f2) that has passed through the axis portion through hole 56d is press fit and coupled to the axis hole 51e of the lower end portion of the coupling rod 51d. An upper end portion of the coupling rod 51d is screwed and coupled to a female screw of a ceiling portion (an upper end portion) of the hat-shape button 51a'. The hat-shape button 51a', the coupling rod 51d, and the slip prevention pin 53f move up and down as an integrated object.

The hat-shape button 51a' is fit and fixed to the rubber button cover 51f, and forms together with the rubber button cover 51f, the pushbutton 51X. The hat-shape button 51a' is slidably fit into the first cylinder 60c. An upper surface of the stopper flange 51c abuts to a lower surface of the inner flange portion 60g of the first cylinder 60c, and thereby, the projection position of the hat-shape button 51a' is regulated. A lower surface of the stopper flange 51c abuts to the pressing position stopper 60, and thereby, the maximum press displacement position of the hat-shape button 51a' is regulated. A length in which the stopper flange 51c can move between the inner flange portion 60g and the pressing position stopper 60 is the stroke L of the pushbutton 51X.

The intermediate spring 54 is inserted to between a lower surface of a ceiling portion of the hat-shape button 51a', and the upper surface of the stopper 55bs of the first switch holder 55b, in a compressed state. The upper surface of the stopper flange 51c abuts to the lower surface of the inner flange portion 60g (or the head portion 53f1 abuts to a periphery portion of the axis portion through hole 56d of the first switch holder 55b), and thereby, projection of the hat-shape button 51a', the coupling rod 51d, and the slip prevention pin 53f is regulated. The projection movement of the hat-shape button 51a' is regulated as described above, and sets the initial elastic force of the intermediate spring 54.

FIG. 15 illustrates an initial state of the two-stage pushbutton switch device 50 of the second modification of the second embodiment. The intermediate spring 57 has the smallest spring constant, and the intermediate spring 54 and the load absorption spring 52 have larger spring constants in this order. The intermediate spring 57 and the intermediate spring 54 have the almost equal initial elastic forces, or the intermediate spring 57 has slightly smaller initial elastic force, and the load absorption spring 52 has the largest initial elastic force.

In the two-stage pushbutton switch device 50 of the illustrated embodiment, in the initial state, when a gap between the stopper flange 51c and the pressing position stopper 60 is set to be the stroke L, a gap between the head portion 53f1 and the operation portion 55s is set to be the stroke L1, and a gap between a pressing portion 56a and an operation portion 58s is set to be the stroke L2, L, L1, and L, L1, and L2 are set to be L>L1>L2.

In the two-stage pushbutton switch device 50 of the present embodiment, when a pressing force (energizing force) of flexing the rubber button cover 51f and pressing and displacing the hat-shape button 51a' (the pushbutton 51X) is applied, when a force of pressing down the hat-shape button 51a' exceeds the initial elastic force of the intermediate spring 57, the hat-shape button 51a' is pressed and displaced while compressing the intermediate spring 57. At that time, the first switch holder 55b and the second pressing member 56' are integrally pressed and displaced (descend), and the pressing portion 56a of the second pressing member 56' approaches, abuts to, and presses (presses down) the operation portion 58s. When the pressing force to the operation portion 58s exceeds the operation force amount of the second switch 58, the second switch 58 is turned on. Since the second switch 58 is fixed, even when the pressing force by the pressing portion 56a increases, the pressing portion 56a (the second pressing member 56') is not pressed and displaced anymore.

On the other hand, a force of pressing (compressing) the intermediate spring 54 by the hat-shape button 51a' increases as the press displacement of the hat-shape button 51a', and exceeds the initial elastic force of the intermediate spring 54 in a stage in which the pressing (compressing) force does not exceed the initial elastic force of the load absorption spring 52, before the second switch 58 is turned on. Accordingly, the hat-shape button 51a' is pressed and displaced with respect to the first switch holder 55b, together with the integral coupling rod 51d and the slip prevention pin 53f while compressing the intermediate spring 54, and the head portion 53f1 approaches the operation portion 55s.

When the pushbutton 51X is further pressed and displaced after the second switch 58 is turned on, the hat-shape button 51a' is further pressed and displaced while compressing the intermediate spring 54, and the head portion 53f1 abuts to the operation portion 55s. When the force of pressing the operation portion 55s by the head portion 53f1 exceeds the operation force amount of the first switch 55, the first switch 55 is turned on.

After that, when the pushbutton 51X is further pressed and displaced, the first switch 55 is pressed and displaced while compressing the load absorption spring 52, the stopper flange 51c abuts to the pressing position stopper 60, and thereby, pressing of the pushbutton 51X is regulated. This regulated position is the maximum press displacement position of the pushbutton 51X.

In the two-stage pushbutton switch device 50 of the present embodiment, the stroke L2 until the second switch 57 is turned on is short (shorter than the difference between the strokes L and L), and a pressing force until the operation force amount is applied is small. On the other hand, the stroke L1 until the first switch 55 is turned on is long and a pressing force until the operation force amount is applied is large. Thus, the second switch 58 can be turned on in a relatively early period. After that, a pressing force that is long in a pressing length until the first switch 55 is turned on, and strong is required. Thus, feeling of turning on the second switch and the first switch 58 can be clearly distinguished.

In the two-stage pushbutton switch device 50 of the present embodiment, projection movements (projection positions) of the hat-shape button 51a', the first switch holder 55b, and the second pressing member 56' are individually regulated. Thus, the initial elastic forces of the intermediate spring 54, the load absorption spring 52, and the intermediate spring 57 can be individually set, each of the strokes L, L1, L2 can be individually and correctly set, the degree of freedom of the setting is high, and versatility of the two-stage pushbutton switch device 50 is excellent.

In the two-stage pushbutton switch device 50 of the present embodiment, the initial elastic force and the spring constant of the intermediate spring 54 are made to be the smallest, and the stroke L1 is made to be the smallest. Then, the first switch 55 and the second switch 58 can be turned on in this order.

In the embodiment described above, the present disclosure is applied to a two-stage pushbutton switch device for an endoscope. However, the present disclosure can be applied also to, more widely, a three or more stage pushbutton switch device by arranging spring means and electrical switch members supported between the spring means in more multiple stages, and setting forces of a plurality of spring means so that the plurality of electrical switch members are sequentially operated.

Figure 16A:
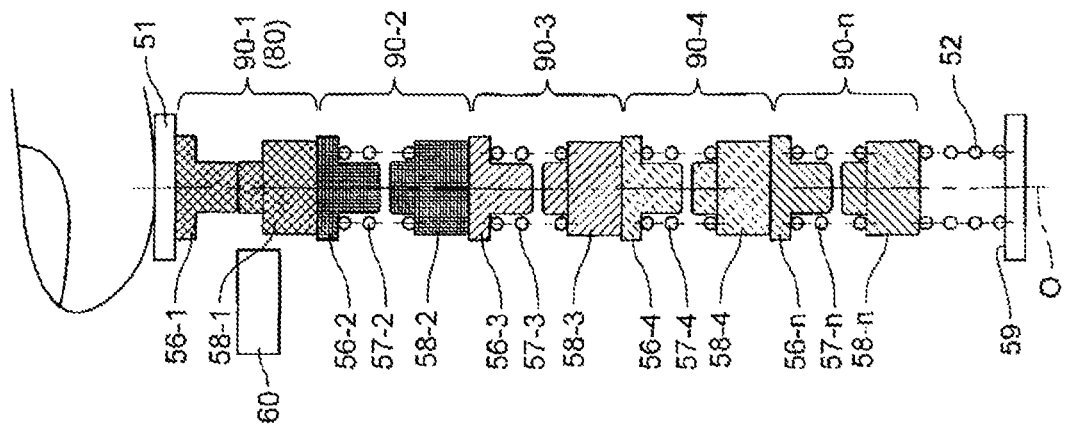
FIG. 16A, FIG. 16B, and FIG. 16C are conceptual diagrams illustrating an embodiment group in which the multistage pushbutton switch device of the present disclosure is generalized.
Figure 16B:
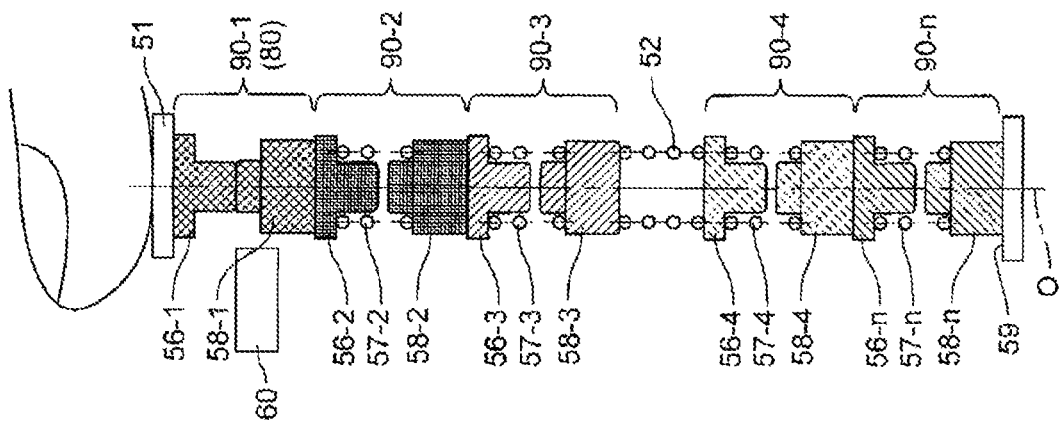
Figure 16C:
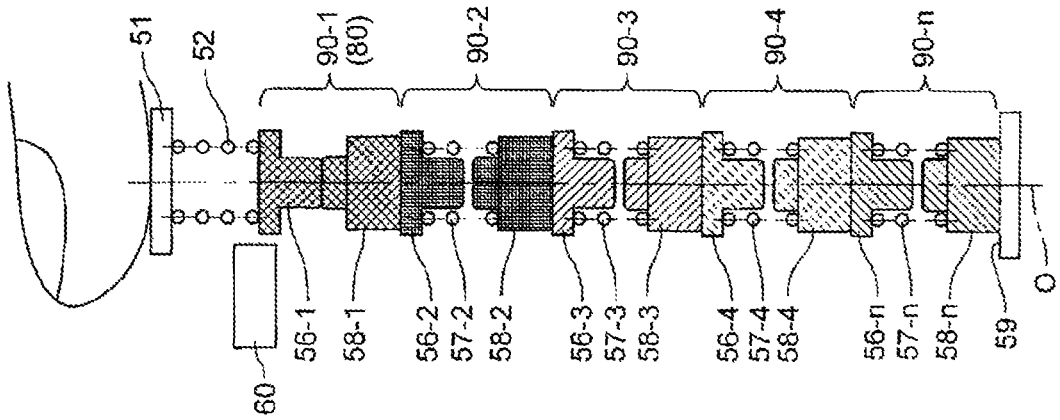

FIG. 16A, FIG. 16B, and FIG. 16C are conceptual diagrams illustrating an embodiment group in which the multistage pushbutton switch device of the present disclosure is generalized. In FIG. 16A, FIG. 16B, and FIG. 16C, n (n is an integer of two or more) pushbutton switches 90-1, 90-2, 90-3, 90-4 . . . 90-n are arranged in between the pushbutton 51 and the reaction force wall 59, in the axial line O. Among the n pushbutton switches 90-n, the pushbutton switch 90-1 that is the nearest to the pushbutton 51 has a pressing member 56-1 and an electrical switch 58-1, and other pushbutton switches 90-n than the pushbutton switch 90-1 have pressing members 56-n, intermediate springs 57-n, and electrical switches 58-n. The pushbutton switch 90-1 corresponds to the first pushbutton switch 80 of the embodiment of FIG. 5 (FIG. 5A, FIG. 5B, FIG. 5C). Hatching having different manners is applied to main components composing each of the pushbutton switches 90-n so that discrimination of each of the pushbutton switches 90-n is facilitated.

In the embodiment of FIG. 16A, the load absorption spring 52 is located in between the pushbutton 51, and the pushbutton switch 90-1 that is the nearest to the pushbutton 51. In the embodiment of FIG. 16B, the load absorption spring 52 is located in between the pushbutton switches 90-3 and 90-4. In the embodiment of FIG. 16C, the load absorption spring 52 is located in between the reaction force wall 59, and the pushbutton switch 90-n that is the nearest to the reaction force wall 59. In the embodiment of FIG. 16B, the load absorption spring 52 is located in between the pushbutton switches 90-3 and 90-4. However, the load absorption spring 52 has a degree of freedom in an arrangement position when the load absorption spring 52 is in between adjacent two pushbutton switches 90-n. In the embodiment of FIG. 16B, the load absorption springs 52 are arranged in a plurality of positions. The load absorption spring 52 can be arranged in any one or more of positions of FIG. 16A to FIG. 16C, theoretically.

In each embodiment of FIG. 16A to FIG. 16C described above, spring forces (spring constants and initial elastic forces) of the load absorption spring 52 and the intermediate spring 57-n are appropriately set. Thereby, n electrical switches 58-n can be sequentially operated by pressing operation of the single pushbutton 51, and the electrical switch 58-n that is turned on lastly can be turned on before the pushbutton 51 abuts to the pressing position stopper 60.

In the embodiment described above, the pushbutton switch 90-1(80) has no intermediate spring. However, as similar to the other pushbutton switches 90-n, the pushbutton switch 90-1(80) may be a type in which the intermediate spring is arranged in between the pressing member 56-1 and the electrical switch 58-1. The pushbutton switch having no intermediate spring may be arranged in other positions than the highest stage. However, in a premise that n electrical switches 58-n having the same operation force amount are used from among the n pushbutton switches 90-n, the pushbutton switch 90-n having no intermediate spring cannot be configured more than one. That is, in (n−1) that is one less than n, or more of the pushbutton switches, an intermediate spring member that separates the electrical switch member and the pressing member is arranged.

INDUSTRIAL APPLICABILITY

The multistage pushbutton switch device for an endoscope according to the present disclosure can be applied to a general endoscope such as an endoscope that sequentially performs any two or more operations of air supply, water supply, and spraying, from a discharge nozzle. The multistage pushbutton switch device of the present disclosure can be applied to a general usage of sequentially turning on a plurality of electrical switches by pressing operation of a pushbutton member.

It is to be noted that, as used herein and in the appended claims, the singular forms "a", "an", and "the" include plural referents unless the context clearly dictates otherwise.

It is to be noted that the disclosed embodiment is illustrative and not restrictive in all aspects. The scope of the present invention is defined by the appended claims rather than by the description preceding them, and all changes that fall within metes and bounds of the claims, or equivalence of such metes and bounds thereof are therefore intended to be embraced by the claims.

The invention claimed is:

1. A multistage pushbutton switch device comprising:
a pushbutton that is energized in a projection direction, and is pressed and displaced against an energizing direction; and
a plurality of electrical switches, each switch composed of a tactile switch that is operated from an off state to an on state by pressing operation of the pushbutton, wherein
n (n is an integer of two or more) pushbutton switches and at least one load absorption spring are arranged between the pushbutton and a reaction force wall receiving a reaction force of an energizer that energizes the pushbutton, in the same axial line, so that elements other than elements that contact with the reaction force wall are movable, each of the n pushbutton switches is composed of an electrical switch and a pusher that operates the electrical switch, and (n−1) that is one less than n, or more pushbutton switches are arranged with an intermediate spring that separates the electrical switch from the pusher, the intermediate spring being located in a same pushbutton switch, when the pushbutton is pressed and displaced, the respective electrical switches of the corresponding n pushbutton switches are sequentially turned on, and pressed by the pusher that moves to approach the electrical switch, a stopper that mechanically regulates the maximum press displacement position of the pushbutton is provided, the at least one load absorption spring is arranged in at least one of a position where the at least one load absorption spring is compressed by the pushbutton and the pushbutton switch that is the nearest to the pushbutton, and a position where the at least one load absorption spring is compressed by the reaction force wall and the pushbutton switch that is the nearest to the reaction force wall, and strengths of (n−1) or more intermediate springs and the at least one load absorption spring are set so that an electrical switch that is turned on lastly is turned on before the pushbutton abuts to the stopper.

2. The multistage pushbutton switch device according to claim 1, wherein:
the intermediate spring of at least one of the pushbutton switches is compressed regardless of whether or not the pushbutton is pressed.

3. The multistage pushbutton switch device according to claim 1, wherein
the n pushbutton switches include one pushbutton switch that is not arranged with the intermediate spring, and (n−1) pushbutton switches that are arranged with the intermediate spring.

4. The multistage pushbutton switch device according to claim 2, wherein
the n pushbutton switches include one pushbutton switch that is not arranged with the intermediate spring, and (n−1) pushbutton switches that are arranged with the intermediate spring.

5. The multistage pushbutton switch device according to claim 1, wherein
all the n pushbutton switches are pushbutton switches that are arranged with the intermediate spring.

6. The multistage pushbutton switch device according to claim 2, wherein
all the n pushbutton switches are pushbutton switches that are arranged with the intermediate spring.

7. The multistage pushbutton switch device according to claim 3, wherein n=2.

8. The multistage pushbutton switch device according to claim 4, wherein n=2.

9. The multistage pushbutton switch device according to claim 5, wherein n=2.

10. The multistage pushbutton switch device according to claim 6, wherein n=2.

11. The multistage pushbutton switch device according to claim 1, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

12. The multistage pushbutton switch device according to claim 2, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

13. The multistage pushbutton switch device according to claim 3, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

14. The multistage pushbutton switch device according to claim 4, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

15. The multistage pushbutton switch device according to claim 5, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

16. The multistage pushbutton switch device according to claim 6, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

17. The multistage pushbutton switch device according to claim 7, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

18. The multistage pushbutton switch device according to claim 8, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

19. The multistage pushbutton switch device according to claim 9, the multistage pushbutton switch device for an endoscope, further comprising
a solenoid valve that performs any two or more operations of air supply, water supply, and spraying, from a discharge nozzle opened in a tip end of an intracorporeal insertion portion, in response to on/off of the plurality of electrical switches.

20. The multistage pushbutton switch device according to claim 10, the multistage pushbutton switch device for an endoscope, further comprising a solenoid valve that performs any two or more operations of air supply, water supply, and spraying, from a discharge nozzle opened in a tip end of an intracorporeal insertion portion, in response to on/off of the plurality of electrical switches.

* * * * *